(12) United States Patent  
Sullivan et al.

(10) Patent No.: US 7,111,502 B2
(45) Date of Patent: Sep. 26, 2006

(54) SYSTEMS AND METHODS FOR REDUCING THE EFFECT OF CORRUPTIVE SIGNALS DURING NANOLITER OSMOMETRY

(75) Inventors: Benjamin Sullivan, La Jolla, CA (US); Eric Donsky, Los Angeles, CA (US)

(73) Assignee: Ocusense, Inc., Los Angeles, CA (US)

(*) Notice: Subject to any disclaimer, the term of this patent is extended or adjusted under 35 U.S.C. 154(b) by 193 days.

(21) Appl. No.: 10/810,780

(22) Filed: Mar. 25, 2004

(65) Prior Publication Data

US 2005/0149275 A1 Jul. 7, 2005

Related U.S. Application Data

(63) Continuation-in-part of application No. 10/400,617, filed on Mar. 25, 2003.

(60) Provisional application No. 60/401,432, filed on Aug. 6, 2002.

(51) Int. Cl.
*G01N 13/04* (2006.01)
(52) U.S. Cl. ...................................... 73/64.47

(58) Field of Classification Search ............... 73/64.47, 73/64.56, 64.41; 324/396
See application file for complete search history.

(56) References Cited

U.S. PATENT DOCUMENTS

| | | | | | |
|---|---|---|---|---|---|
| 4,269,197 | A | * | 5/1981 | Gilbard | 600/576 |
| 4,951,683 | A | * | 8/1990 | Davis | 600/383 |
| 4,996,993 | A | * | 3/1991 | York | 600/547 |
| 5,005,403 | A | * | 4/1991 | Steudle et al. | 73/61.71 |
| 5,143,080 | A | * | 9/1992 | York | 600/549 |
| 5,461,699 | A | * | 10/1995 | Arbabi et al. | 706/21 |
| 5,665,904 | A | * | 9/1997 | Boling | 73/64.47 |

\* cited by examiner

*Primary Examiner*—Hezron Williams
*Assistant Examiner*—Ryan Christensen
(74) *Attorney, Agent, or Firm*—Baker & McKenzie LLP

(57) ABSTRACT

An osmolarity measuring system includes the ability to recognize patterns within the electrical profile of nanoliters of fluid an account for corruptive signals in the electrical profile. These corruptive signals are mainly caused by the mechanical relaxation of the sample fluid after delivery or evaporation across the electrodes.

24 Claims, 19 Drawing Sheets

SYSTEMS AND METHODS FOR REDUCING THE EFFECT OF CORRUPTIVE SIGNALS DURING NANOLITER OSMOMETRY

RELATED APPLICATIONS INFORMATION

This application claims priority as a continuation-in-part under 35 U.S.C. §120 to related application Ser. No. 10/400,617, entitled "Tear Film Osmometry," filed on Mar. 25, 2003, which claims priority under 35 U.S.C. § 119 to U.S. Provisional Patent Application Ser. No. 60/401,432, filed on Aug. 6, 2002. This application is also related to: U.S. patent application Ser. No. 10/772,084, entitled "Systems And Methods For Calibrating Osmolarity Measuring Devices," filed on Feb. 3, 2004; U.S. patent application Ser. No. 10/718,498, entitled, "Systems and Methods For Measuring Tear Film Osmolarity," filed Nov. 19, 2003; and U.S. patent application Ser. No. 10/800,398, entitled, "Systems and Methods For Delivering A Sample Fluid To A Receiving Substrate," filed Mar. 12, 2004; and U.S. patent application Ser. No. 10/800,392, entitled "Systems and Methods For Collecting And Analyzing Tear Film Osmolarity Data," filed Mar. 12, 2004, each of which is incorporated herein by reference in its entirety as if set forth in full.

BACKGROUND

1. Field of the Inventions

The present invention relates generally to measuring the osmolarity of fluids and, more particularly, to measuring the osmolarity of tear film and to methods of more accurately obtaining such measurements.

2. Background Information

Tears fulfill an essential role in maintaining ocular surface integrity, protecting against microbial challenge, and preserving visual acuity. These functions, in turn, are critically dependent upon the composition and stability of the tear film structure, which includes an underlying mucin foundation, a middle aqueous component, and an overlying lipid layer. Disruption, deficiency, or absence of the tear film can severely impact the eye. If unmanaged with artificial tear substitutes or tear film conservation therapy, these disorders can lead to intractable desiccation of the corneal epithelium, ulceration and perforation of the cornea, an increased incidence of infectious disease, and ultimately pronounced visual impairment and blindness.

Keratoconjunctivitis sicca ("KCS"), or "dry eye", is a condition in which one or more of the tear film structure components listed above is present in insufficient volume or is otherwise out of balance with the other components. It is known that the fluid tonicity or osmolarity of tears increases in patients with KCS. KCS is associated with conditions that affect the general health of the body, such as Sjogren's syndrome, aging, and androgen deficiency. Therefore, osmolarity of a tear film can be a sensitive and specific indicator for the diagnosis of KCS and other conditions.

The osmolarity of a sample fluid (e.g., a tear) can be determined by an ex vivo technique called "freezing point depression," in which solutes or ions in a solvent (i.e. water), cause a lowering of the fluid freezing point from what it would be without the ions. In the freezing point depression analysis the freezing point of the ionized sample fluid is found by detecting the temperature at which a quantity of the sample (typically on the order of about several milliliters) first begins to freeze in a container (e.g., a tube). To measure the freezing point, a volume of the sample fluid is collected into a container, such as a tube. Next, a temperature probe is immersed in the sample fluid, and the container is brought into contact with a freezing bath or Peltier cooling device. The sample is continuously stirred so as to achieve a supercooled liquid state below its freezing point. Upon mechanical induction, the sample solidifies, rising to its freezing point due to the thermodynamic heat of fusion. The deviation of the sample freezing point from 0° C. is proportional to the solute level in the sample fluid. This type of measuring device is sometimes referred to as an osmometer.

Presently, freezing point depression measurements are made ex vivo by removing tear samples from the eye using a micropipette or capillary tube and measuring the depression of the freezing point that results from heightened osmolarity. However, these ex vivo measurements are often plagued by many difficulties. For example, to perform freezing point depression analysis of the tear sample, a relatively large volume must be collected, typically on the order of 20 microliters (μL) of a tear film. Because no more than about 10 to 100 nanoliters (nL) of tear sample can be obtained at any one time from a KCS patient, the collection of sufficient amounts of fluid for conventional ex vivo techniques requires a physician to induce reflex tearing in the patient. Reflex tearing is caused by a sharp or prolonged irritation to the ocular surface, akin to when a large piece of dirt becomes lodged in one's eye. Reflex tears are more dilute, i.e. have fewer solute ions than the tears that are normally found on the eye. Any dilution of the tear film invalidates the diagnostic ability of an osmolarity test for dry eye, and therefore make currently available ex vivo methods prohibitive in a clinical setting.

A similar ex vivo technique is vapor pressure osmometry, where a small, circular piece of filter paper is lodged underneath a patient's eyelid until sufficient fluid is absorbed. The filter paper disc is placed into a sealed chamber, whereupon a cooled temperature sensor measures the condensation of vapor on its surface. Eventually the temperature sensor is raised to the dew point of the sample. The reduction in dew point proportional to water is then converted into osmolarity. Because of the induction of reflex tearing and the large volume requirements for existing vapor pressure osmometers, they are currently impractical for determination of dry eye.

The Clifton Nanoliter Osmometer (available from Clifton Technical Physics of Hartford, N.Y., USA) has been used extensively in laboratory settings to quantify the solute concentrations of KCS patients, but the machine requires a significant amount of training to operate. It generally requires hour-long calibrations and a skilled technician in order to generate acceptable data. The Clifton Nanoliter Osmometer is also bulky and relatively expensive. These characteristics seriously detract from its use as a clinical osmometer.

In contrast to ex vivo techniques that measure osmolarity of tear samples removed from the ocular surface, an in vivo technique that attempted to measure osmolarity directly on the ocular surface used a flexible pair of electrodes that were placed directly underneath the eyelid of the patient. The electrodes were then plugged into an LCR meter to determine the conductivity of the fluid surrounding them. While it has long been known that conductivity is directly related to the ionic concentration, and hence osmolarity of solutions, placing the sensor under the eyelid for half a minute likely induced reflex tearing. Furthermore, these electrodes were difficult to manufacture and posed increased health risks to the patient as compared to simply collecting tears with a capillary.

It should be apparent from the discussion above that current osmolarity measurement techniques are unavailable in a clinical setting and cannot attain the volumes necessary for dry eye patients. Thus, there is a need for an improved, clinically feasible, nanoliter-scale, precise osmolarity measurement that can adjust to eliminate the effects of corrupting signals. The present invention satisfies this need.

SUMMARY OF THE INVENTION

Osmolarity measurement of a sample fluid, such as a tear film, is achieved by depositing an aliquot volume of the sample fluid on a microchip having a substrate and a sample region of the substrate, wherein the volume of the sample fluid operatively covers a sufficient portion of the sample region such that the energy imparted to the sample fluid is detected from the sample region to produce an output signal that indicates osmolarity of the sample fluid. Thus, an osmolarity measurement of the sample fluid can be obtained from the detected energy of the sample volume. The aliquot-sized sample volume can be quickly and easily obtained, even from dry eye patients. An aliquot volume can comprise, for example, a volume of no more than 20 microliters ($\mu L$), but can be as little as 1 nL. An osmolarity sensor system can receive the microchip and sample volume, and can detect energy from the sample volume to display an accurate osmolarity measurement. In this way, a reliable osmolarity measurement can be obtained with minimum inconvenience and discomfort to a patient, without requiring a great deal of skill to obtain the measurement, and with a high degree of repeatability and accuracy.

In one aspect, corruptive signals that effect detection of the energy imparted to the sample fluid are addressed and handled such that accurate measurements can be obtained for sample sizes in which physical phenomena dominate the electrical profile of the sample over time. For example, the transient relaxation of an aliquot of fluid across the measuring electrodes can be modeled to separate mechanical effects on the measured voltage from the steady state electrical conductivity which relates to osmolarity. Further, the effect of evaporation, which is an unavoidable consequence of fluidic systems with an inherent air gap, whether the receiving substrate be comprised of top down array microchips, or microchannel systems with a dead volume, etc., can be accounted for using linear regression and curve fitting techniques.

These and other aspects, features and advantages are explained more fully in the section entitled "Detailed Description of the Preferred Embodiments."

BRIEF DESCRIPTION OF THE DRAWINGS

Features, aspects, and embodiments of the inventions are described in conjunction with the attached drawings, in which.

DETAILED DESCRIPTION OF THE PREFERRED EMBODIMENTS

Figure 1:
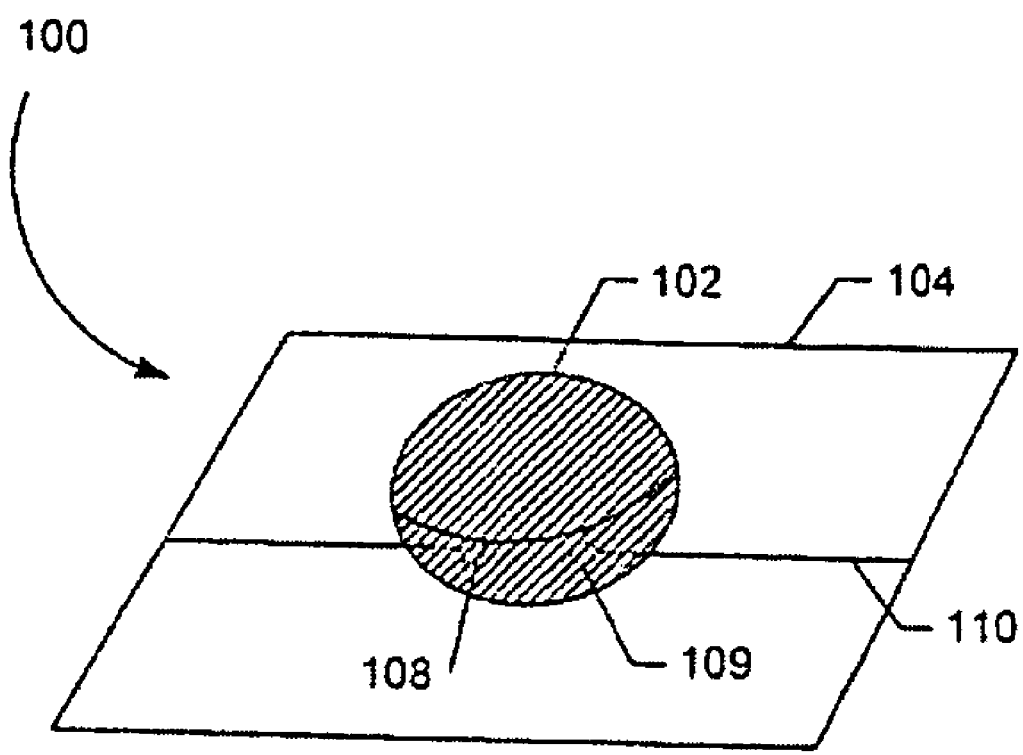
FIG. 1 illustrates an aliquot-sized sample receiving chip for measuring the osmolarity of a sample fluid.

Using the systems and methods described herein, a sample fluid volume can be easily deposited on a substrate sample region of a measurement chip. Energy can then be transferred to the sample fluid, such that energy properties of the sample fluid can be detected to provide an accurate measurement of sample osmolarity. The energy transferred can comprise electrical energy. For example, electrodes associated with the substrate can be spaced such that an aliquot-sized sample volume can bridge at least two of the electrodes. Electrical energy passing through the electrodes can be used to measure conductivity which can be correlated with, or used to find, an osmolarity measure.

As the feature size of the electrodes has been made on length scales amenable to the volumes of interest, it has become possible to deposit raw, unprocessed fluid samples directly into the microchip. No dilution or special vacuum chambers are necessary. When coupled with high frequency AC signals to overcome electrolysis problems, it has become feasible to measure osmolarity quickly and inexpensively with commodity hardware. It should be noted that eliminating the need for dilution or special vacuum chambers allows for the development of small, inexpensive test devices. In other words, by using the systems and methods described below, the normally debilitating effect of an air gap over the measuring electrodes can be minimized. In fact, as will be explained, even more accurate measurements than previously before possible can be made, even in the presence of the corruptive signals, attributable to the presence of an air gap. Therefore, it is the ability to overcome these corruptive signals that can enable small, cost effective measurement devices can produce highly accurate measurements as described below.

Thus, as just explained, the ability to overcome these corruptive signals is necessary to achieve accurate measurements using the systems and methods described herein. For example, when nanoliters of fluid are deposited onto a microelectrode array, the conductivity of the sample can be recorded when placed in series with a voltage divider or auto-balancing bridge. When the fluid is deposited, however, the signals produced are often erratic and initially do not accurately record the relevant properties of the sample. As such, it is important to eliminate these transient signals and focus on the resulting voltage produced after the sample has equilibrated. This task often requires two steps as explained in detail below. First, the system determines at which point the sample was placed. Second, the system must determine the osmolarity of the sample at the time of placement, which cannot be done simply by using the reading at that point for the reasons stated above.

If one were attempting to perform this task by viewing the voltage trace, the point at which the sample was placed would be seen as a spike in the trace. The derivative at this point will be greater in value than the derivative at any other point on the trace. Therefore, from a computational standpoint, the system should take the derivative of the voltage signal to determine the point at which the sample was placed. The point at which the derivative is at its maximum will be the relevant point.

Once the time at which the sample was placed has been determined, the system can be configured to fit a curve to the rest of the data. Upon fitting this curve, it can be extrapolated back to the point at which the sample was placed. In this way, the shape of the curve resulting from evaporation of the sample over time can be used to calculate the earlier voltage. Fluidic delivery into the microchip will always create corruptive signals arising after the initial placement spike.

In large part, this is due to the presence of the air gap. Because of the air gap, the sample does not come smoothly into contact with measuring electrodes. Rather, there is "jostling", as the sample settles on to the measuring electrodes. This jostling creates mechanical effects that show up as corruptive signals. As is well known, such corruptive signals can often comprise a ringing nature and can be referred to as "ringing signals." Such a corruptive ringing signal will die out after a certain amount of time. Thus, the system can be configured to calculate the amount of time it will take the ringing signals to settle based on the measured properties of the voltage signal. In the alternative, the machine will wait a preset amount time, e.g., around 100 ms, after the initial spike in voltage, before fitting a line to the steady state. This can, depending on the embodiment, allow a simpler implementation overall.

As mentioned, a second problem that impacts the ability to make accurate measurements is evaporation. As the sample begins to evaporate completely, i.e. when it breaks into dry patches on top of the measuring electrodes, the conductivity will fall off exponentially. This skews the overall average and precludes algorithms from arbitrarily averaging after the sample has been placed. Moreover, some samples are so small that the relaxation dynamics may not have died out before the sample starts to critically evaporate. By modeling the transient relaxation, we can account for these effects.

Therefore, a key issue in determining osmolarity is deciding which time and length scales are most appropriate for analysis, as well as pinpointing the exact time of drop placement.

Before describing the systems and methods for dealing with corruptive signals, exemplary embodiments are described for measuring the osmolarity of an aliquot volume of a sample fluid, e.g., tear film, sweat, blood, or other fluids. The exemplary embodiments are configured to be relatively fast, non-invasive, inexpensive, and easy to use, with minimal risk of injury to the patient. Accurate measurements can be provided with as little as nanoliter volumes of a sample fluid. For example, a measuring device configured in accordance with the invention enables osmolarity measurement with no more than 1 mL of sample fluid, and typically much smaller volumes can be successfully measured. In one embodiment described further below, osmolarity measurement accuracy is not compromised by variations in the volume of sample fluid collected, so that osmolarity measurement is substantially independent of collected volume. The sample fluid can include tear film, sweat, blood, or other bodily fluids. It should be noted, however, that sample fluid can comprise other fluids, such as milk or other beverages.

FIG. 1 illustrates an exemplary embodiment of an osmolarity chip 100 that can be used to measure the osmolarity of a sample fluid 102, such as a tear film sample. In the FIG. 1 embodiment, the chip 100 includes a substrate 104 with a sample region having sensor electrodes 108 and 109 and circuit connections 110 imprinted on the substrate. The electrodes may be enclosed within a series of microchannels to protect against evaporation. The electrodes and circuit connections are preferably printed using well-known photolithographic techniques. For example, current techniques enable the electrodes 108 and 109 to have a diameter in the range of approximately one (1) to eighty (80) microns, spaced apart sufficiently so that no conductive path exists in the absence of sample fluid. Currently available techniques, however, can provide electrodes of less than one micron in diameter, and these are sufficient for a chip constructed in accordance with the invention. The amount of sample fluid needed for measurement is no more than is necessary to extend from one electrode to the other, thereby providing an operative conductive path. The photolithographic scale of the chip 100 permits the measurement to be made for aliquot-sized samples in a micro or nano-scale level. For example, reliable osmolarity measurement can be obtained with a sample volume of less than 20 µL of tears. A typical sample volume is less than one hundred nanoliters (100 nL). It is expected that it will be relatively easy to collect 10 nL of a tear film sample even from patients suffering from dry eye.

Once the fluid has been transported to the electrodes, whether through adjacent microchannels or by a top down delivery method, the chip 100 is configured to transfer energy to the sample fluid 102, and enable detection of the sample fluid energy properties. In this regard, a current source is applied across the electrodes 108 and 109 through the connections 110. The osmolarity of the sample fluid can be measured by sensing the energy transfer properties of the sample fluid 102. The energy transfer properties can include, for example, electrical conductivity, such that the impedance of the sample fluid is measured, given a particular amount of electrical power (e.g., current) that is transferred into the sample through the connections 110, and electrodes 108 and 109.

If conductivity of the sample fluid is to be measured, then preferably a sinusoidal signal on the order of ten volts at approximately 100 kHz is applied. The real and imaginary parts of the complex impedance of the circuit path from one electrode 108 through the sample fluid 102 to the other electrode 109 are measured. At the frequencies of interest, it is likely that the majority of the electrical signal will be in the real half of the complex plane, which reduces to the conductivity of the sample fluid. This electrical signal (hereafter referred to as conductivity) can be directly related to the ion concentration of the sample fluid 102, and the osmolarity can be determined. Moreover, if the ion concentration of the sample fluid 102 changes, the electrical conductivity and the osmolarity of the fluid will change in a corresponding manner. Therefore, the osmolarity is reliably obtained. In addition, because the impedance value does not depend on the volume of the sample fluid 102, the osmolarity measurement can be made substantially independent of the sample volume.

As an alternative to the input signal described above, more complex signals can be applied to the sample fluid whose response will contribute to a more thorough estimate of osmolarity. For example, calibration can be achieved by measuring impedances over a range of frequencies. These impedances can be either simultaneously (via combined waveform input and fourier decomposition) or sequentially measured. The frequency versus impedance data will provide information about the sample and the relative performance of the sample fluid measurement circuit.

Figure 2:
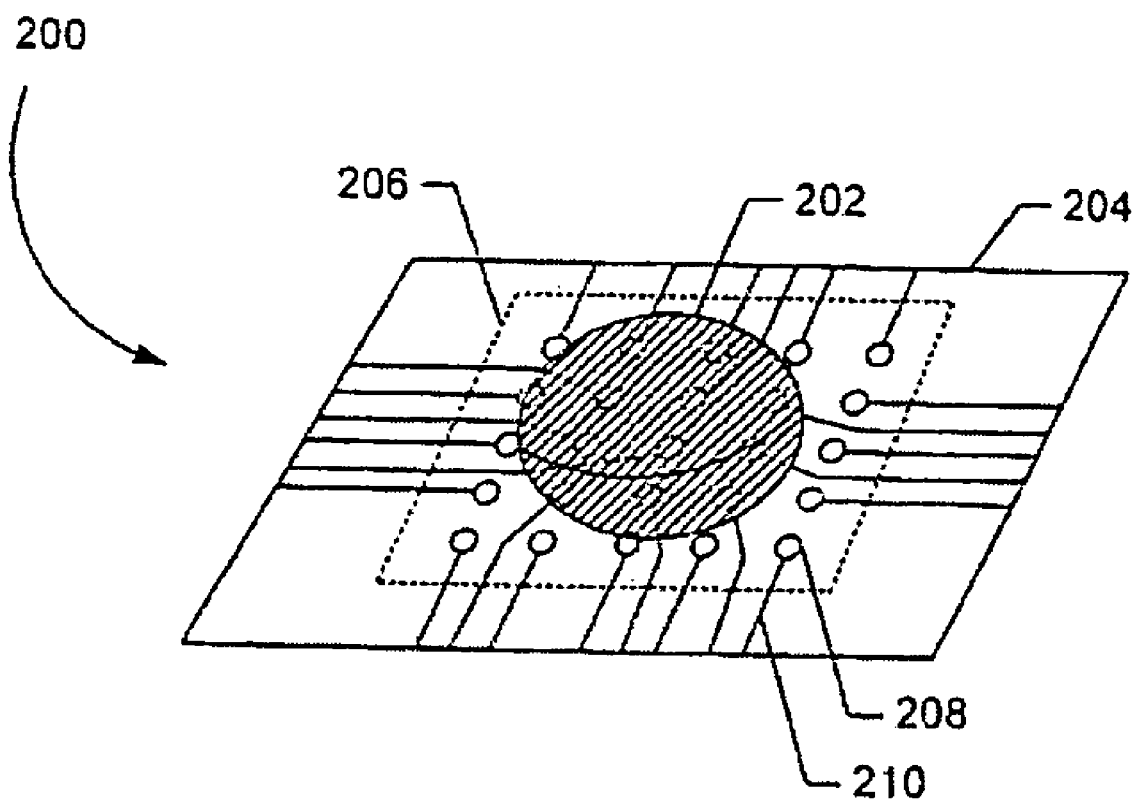
FIG. 2 illustrates an alternative embodiment of a sample receiving chip that includes a circuit region with an array of electrodes imprinted with photolithography techniques.

FIG. 2 illustrates an alternative embodiment of a sample receiving chip 200 that measures osmolarity of a sample fluid 202, wherein the chip comprises a substrate layer 204 with a sample region 206 comprising an imprinted circuit that includes an array of electrodes 208. In the illustrated embodiment of FIG. 2, the sample region 206 has a 5-by-5 array of electrodes that are imprinted with photolithographic techniques, with each electrode 208 having a connection 210 to one side of the substrate 204. Not all of the electrodes 208 in FIG. 2 are shown with a connection, for simplicity of illustration. The electrodes provide measurements to a separate processing unit, described further below.

The electrode array of FIG. 2 provides a means to measure the size of the tear droplet 202, by detecting the extent of conducting electrodes 208, to thereby determine the extent of the droplet. In particular, processing circuitry can determine the number of electrodes that are conducting, and therefore the number of adjacent electrodes that are covered by the droplet 202 will be determined. The planar area of the substrate that is covered by the sample fluid is thereby determined. With a known nominal surface tension of the sample fluid, the height of the sample fluid volume over the planar area can be reliably estimated, and therefore the volume of the droplet 202 can be determined.

Figure 3:
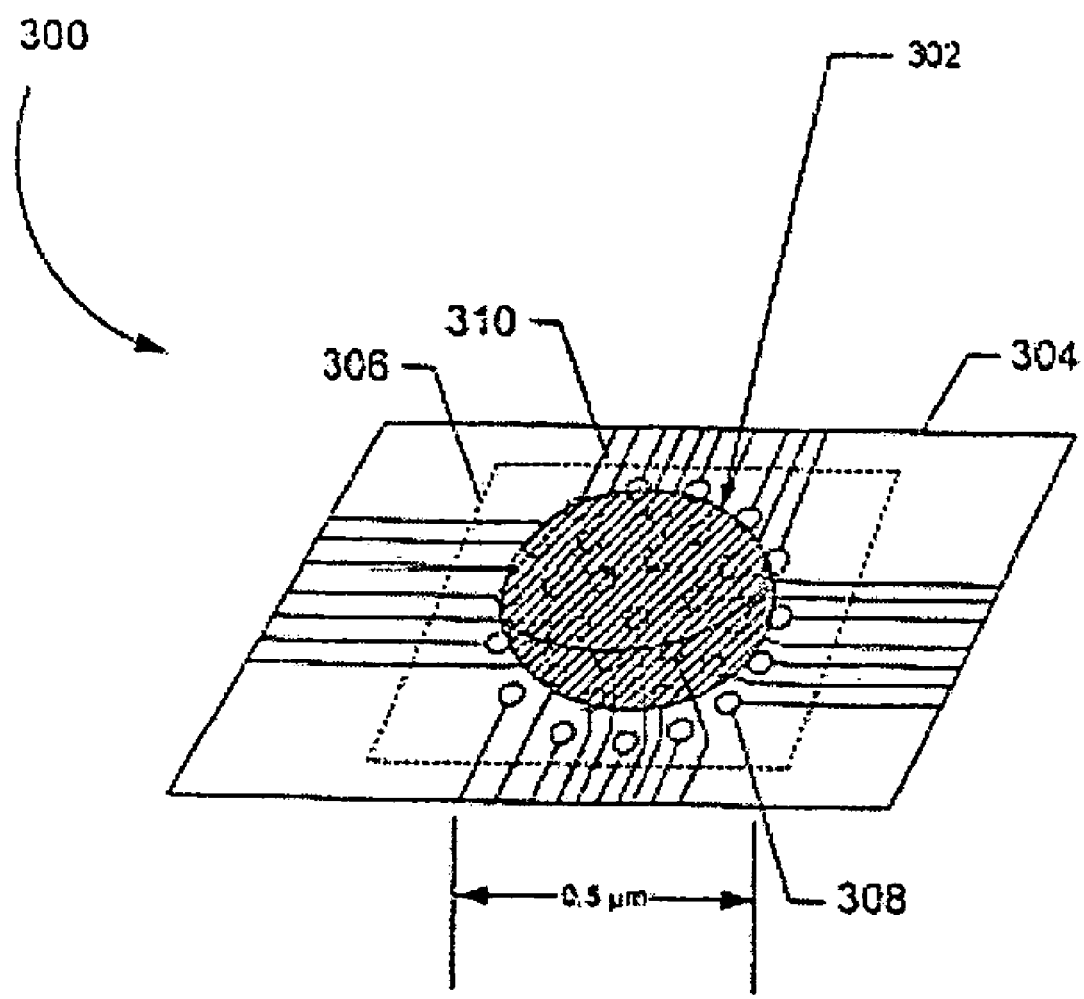
FIG. 3 illustrates another alternative embodiment of the FIG. 1 chip, wherein a circuit region includes printed electrodes arranged in a plurality of concentric circles.

FIG. 3 illustrates another alternative embodiment of a sample receiving chip 300, on which a sample fluid 302 is deposited. The chip comprises a substrate layer 304, wherein a sample region 306 is provided with electrodes 308 that are configured in a plurality of concentric circles. In a manner similar to the square array of FIG. 2, the circular arrangement of the FIG. 3 electrodes 308 also provides an estimate of the size of the sample fluid volume 302 because the droplet typically covers a circular or oval area of the sample region 302. Processing circuitry can detect the largest (outermost) circle of electrodes that are conducting, and thereby determine a planar area of coverage by the fluid sample. As before, the determined planar area provides a volume estimate, in conjunction with a known surface tension, and corresponding volume height of the sample fluid 302. In the FIG. 3 illustrated embodiment, the electrodes 308 can be printed using well known photolithography techniques that currently permit electrodes to have a diameter in the range of one (1) to eighty (80) microns. This allows the submicroliter droplet to substantially cover the electrodes. The electrodes can be printed over an area sized to receive the sample fluid, generally covering 1 mm$^2$ to 1 cm$^2$, or be contained alongside the walls of a microchannel of far smaller dimension, i.e. on the order of 50 μm in width and a few hundred μm in length with the array of electrodes alongside the walls or floor of the channel. The larger configuration would be more amenable to food processing technologies that don't have the volume constraints of clinical tear collection.

The electrodes and connections shown in FIG. 1, FIG. 2, and FIG. 3 can be imprinted on the respective substrate layers as electrodes with contact pads, using photolithographic techniques. For example, the electrodes can be formed with different conductive metalization such as aluminum, platinum, titanium, titanium-tungsten, and other similar material. In one embodiment, the electrodes can be formed with a dielectric rim to protect field densities at the edges of the electrodes. This can reduce an otherwise unstable electric field at the rim of the electrode.

Figure 4:
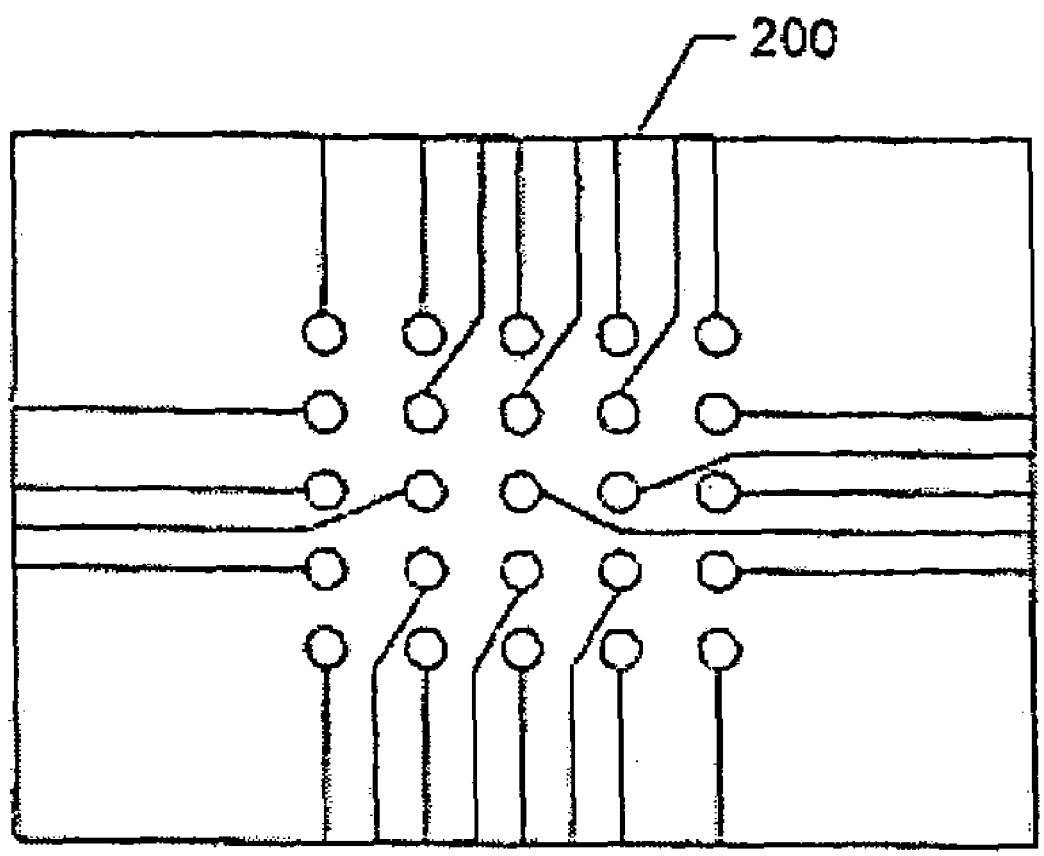
FIG. 4 is a top view of the chip shown in FIG. 2.
Figure 5:
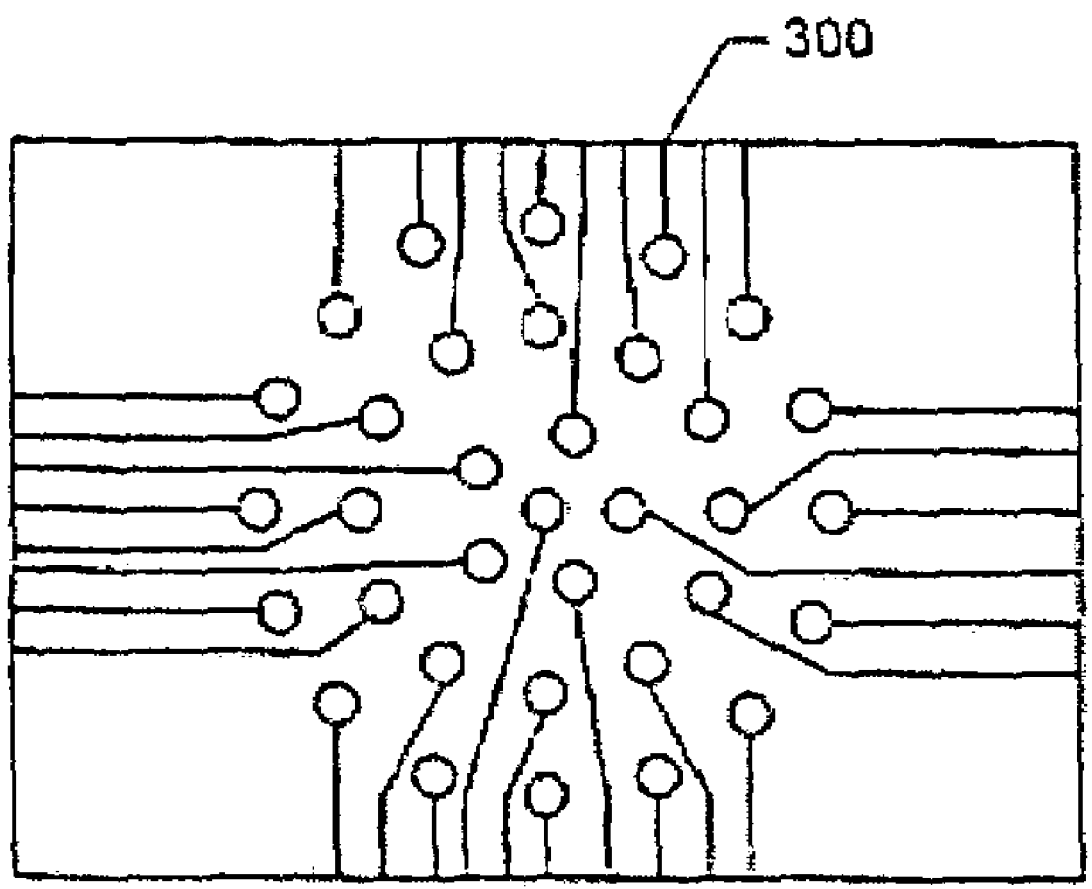
FIG. 5 is a top view of the chip shown in FIG. 3.

Top views of the exemplary embodiments of the chips 200 and 300 are illustrated in FIG. 4 and FIG. 5, respectively. The embodiments show the detailed layout of the electrodes and the connections, and illustrate how each electrode can be electrically connected for measuring the electrical properties of a sample droplet. As mentioned above, the layout of the electrodes and the connections can be imprinted on the substrates 100, 200, 300 and using well-known photolithographic techniques.

Figure 6:
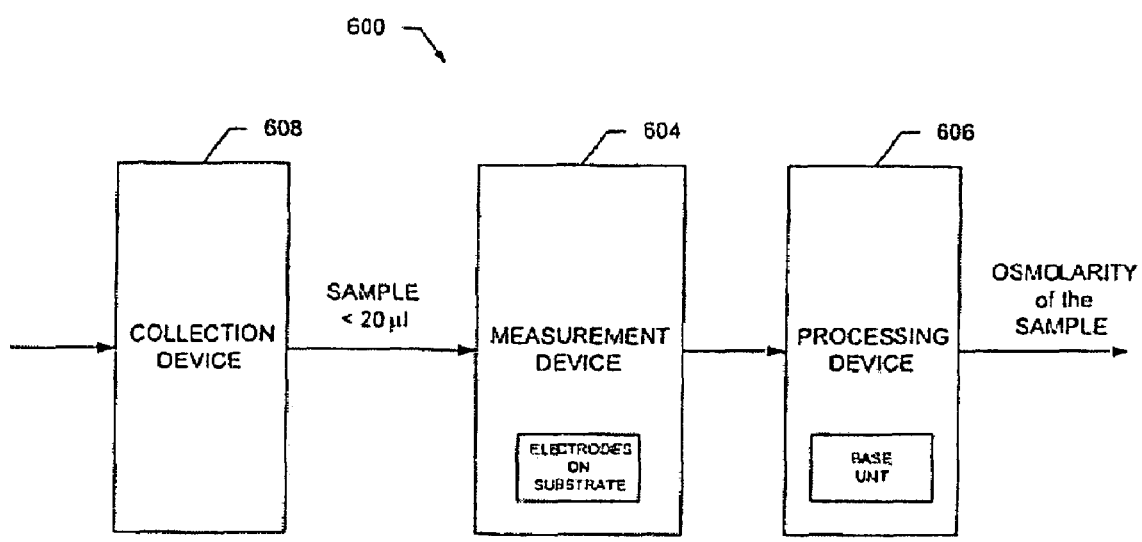
FIG. 6 is a block diagram of an osmolarity measurement system configured in accordance with the present invention.

FIG. 6 is a block diagram of an osmometry system 600 configured in accordance with an embodiment of the present invention. The system 600 in FIG. 6 illustrates determined and used in a process that determines osmolarity of a sample fluid. The osmometry system 600 includes a measurement device 604 and a processing device 606. The measurement device receives a volume of sample fluid from a collection device 608. The collection device can comprise, for example, a micropipette or capillary tube. The collection device 608 collects a sample tear film of a patient, such as by using negative pressure from a fixed-volume micropipette or charge attraction from a capillary tube to draw a small tear volume from the vicinity of the ocular surface of a patient.

The measurement device 604 can comprise a system that transfers energy to the fluid in the sample region and detects the imparted energy. For example, the measurement device 604 can comprise circuitry that provides electrical energy in a specified waveform (such as from a function generator) to the electrical path comprising two electrodes bridged by the sample fluid. The processing device 606 detects the energy imparted to the sample fluid and determines osmolarity. The processing device can comprise, for example, a system including an multimeter that produces data relating to the reactance of the fluid that forms the conductive path between two electrodes, and including a processor that determines osmolarity through a table look-up scheme. If desired, the processing device can be housed in a base unit that receives one of the chips described above.

As mentioned above, a sample sufficient to provide an osmolarity measurement can contain less than 20 microliters (μL) of fluid. A typical sample of tear film in accordance with the invention is collected by a fluid collector such as a capillary tube, which often contains less than one microliter of tear film. Medical professionals will be familiar with the use of micropipettes and capillary tubes, and will be able to easily collect the small sample volumes described herein, even in the case of dry eye sufferers.

The collected sample fluid is expelled from the collection device 608 to the measurement device 604. The collection device can be positioned above the sample region of the chip substrate either manually by a medical professional or by being automatically guided over the sample region. In one embodiment, for example, the collection device (e.g., a capillary tube) is mechanically guided into position with an injection-molded plastic hole in a base unit, or is fitted to a set of clamps with precision screws (e.g., a micromanipulator with needles for microchip interfaces). In another embodiment, the guide is a computer-guided feedback control circuitry that holds the capillary tube and automatically lowers it into the proper position such that the contents of the capillary can be dispensed through a valve into the microchannels and then onto the electrode array.

The electrodes and connections of the chips measure energy properties of the sample fluid, such as conductivity, and enable the measured properties to received by the processing device 606. The measured energy properties of the sample fluid include electrical conductivity and can also include other parameters, such as both parts of the complex impedance of the sample, the variance of the noise in the output signal, and the measurement drift due to resistive heating of the sample fluid. The measured energy properties are processed in the processing device 606 to provide the osmolarity of the sample. In one embodiment, the processing device 606 comprises a base unit that can accept a chip and can provide electrical connection between the chip and the processing device 606. In another embodiment, the base unit can include a display unit for displaying osmolarity values. It should be noted that the processing device 606 and, in particular, the base unit can be a hand-held unit.

Figure 7:
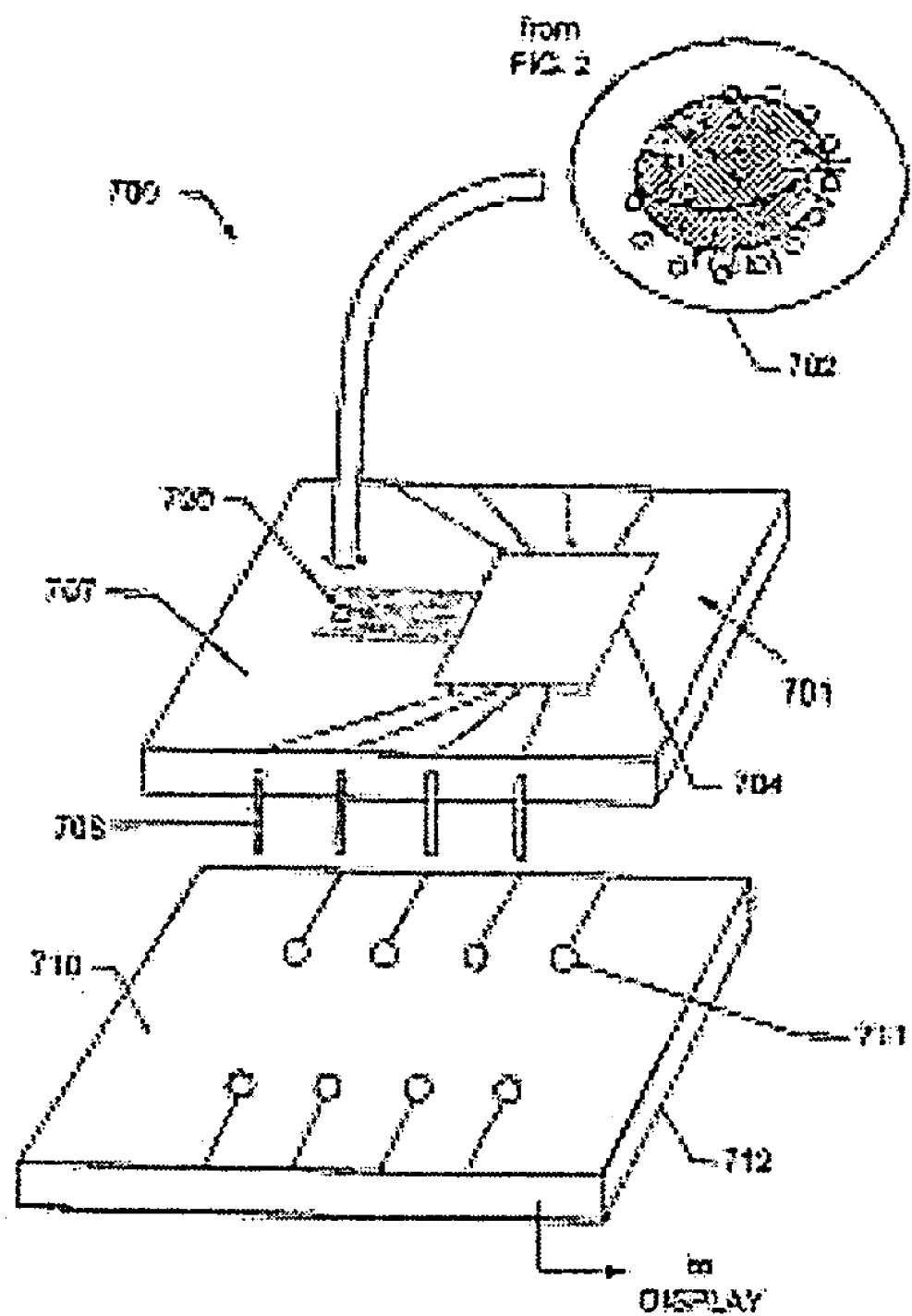
FIG. 7 is a perspective view of a tear film osmolarity measurement system constructed in accordance with the present invention.

FIG. 7 is a perspective view of a tear film osmolarity measuring system 700 constructed in accordance with the present invention. In the illustrated embodiment of FIG. 7, the exemplary system 700 includes a measuring unit 701 that comprises a chip, such as one of the chips described above, and a connector or socket base 710, which provides the appropriate measurement output. The system 700 determines osmolarity by measuring electrical conductivity of the sample fluid. Therefore, the measurement unit 701 comprises a semiconductor integrated circuit (IC) chip with a substrate having a construction similar to that of the chips described above in connection with FIG. 1 through FIG. 5. Thus, the chip 701 includes a substrate layer with a sample region that is defined by at least two electrodes printed onto the substrate layer (such details are of a scale too small to be visible in FIG. 7; see FIG. 1 through FIG. 5). The substrate and sample region are encased within an inert package, in a manner that will be known to those skilled in the art. In particular, the chip 701 is fabricated using conventional semiconductor fabrication techniques into an IC package 707, that includes electrical connection legs 708 that permit electrical signals to be received by the chip 701 and output to be communicated outside of the chip. The packaging 707 provides a casing that makes handling of the chip more convenient and helps reduce evaporation of the sample fluid. This casing can include a top layer or valve of silicon rubber, i.e. PDMS or the like, which can serve to couple the capillary flow into the microchannels of the chip.

Figure 8:
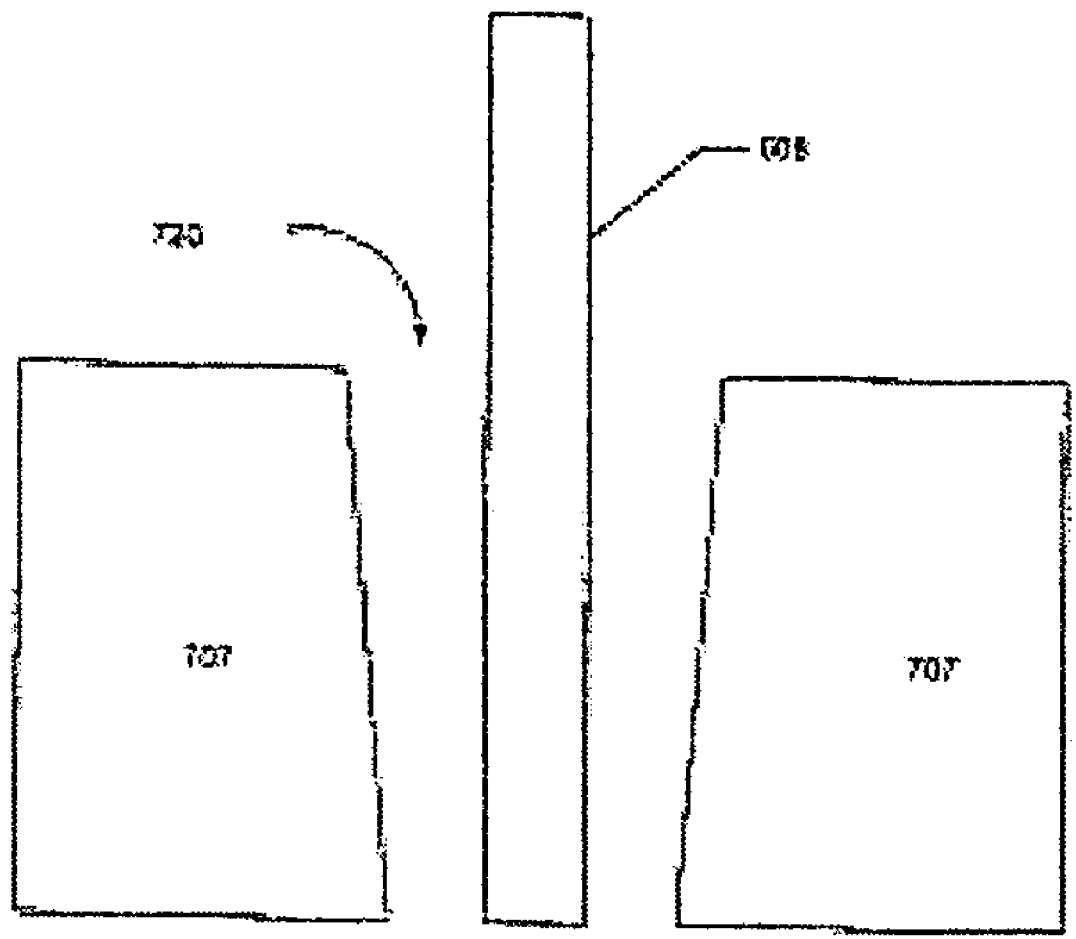
FIG. 8 is a side section of the sample receiving chip showing the opening in the exterior packaging.
Figure 8:
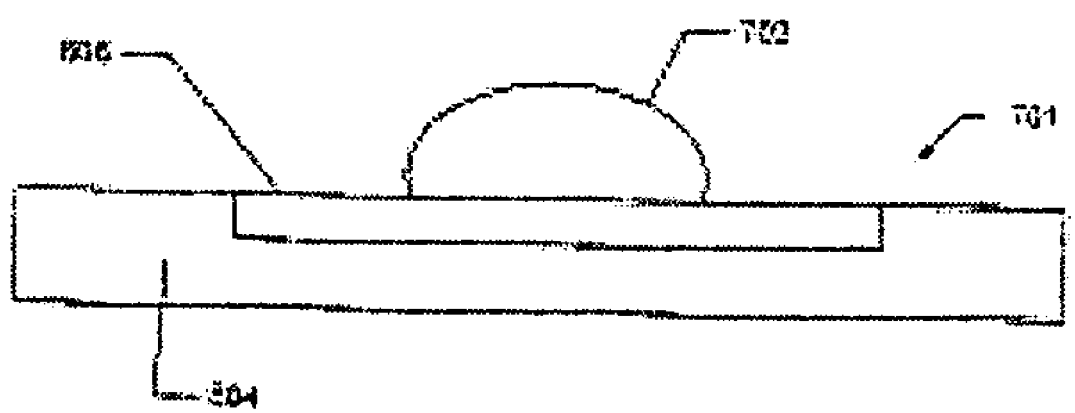

FIG. 8 shows that the measurement chip 701 is fabricated with an exterior opening hole 720 into which the sample fluid 702 is inserted. Thus, the hole 720 can be formed in the semiconductor packaging 707 to provide a path through the chip exterior to the substrate 804 and the sample region 806. The collection device (such as a micropipette or capillary tube) 808 is positioned into the hole 720 such that the sample fluid 702 is expelled from the collection device directly onto the sample region 806 of the substrate 804. The hole 720 is sized to receive the tip of the collection device. The hole 720 forms an opening or funnel that leads from the exterior of the chip onto the sample region 806 of the substrate 804. In this way, the sample fluid 702 is expelled from the collection device 808 and is deposited directly on the sample region 806 of the substrate 804. The sample region is sized to receive the volume of sample fluid from the collection device. In FIG. 8, for example, the electrodes form a sample region 806 that is generally in a range of approximately 1 $mm^2$ to 1 $cm^2$ in area, or be contained alongside the walls of a microchannel of far smaller dimension, i.e. on the order of 50 μm in width and a few hundred μm in length with the array of electrodes alongside the walls or floor of the channel.

Returning to FIG. 7, the chip 701 can include processing circuitry 704 that comprises, for example, a function generator that generates a signal of a desired waveform, which is applied to the sample region electrodes of the chip, and a voltage measuring device to measure the root-mean-square (RMS) voltage value that is read from the chip electrodes. The function generator can produce high frequency alternating current (AC) to avoid undesirable direct current (DC) effects for the measurement process. The voltage measuring device can incorporate the functionality of an (Resistor Inductor Capacitor) RLC measuring device. Thus, the chip 701 can incorporate the measurement circuitry as well as the sample region electrodes. The processing circuitry can include a central processing unit (CPU) and associated memory that can store programming instructions (such as firmware) and also can store data. In this way, a single chip can include the electrodes and associated connections for the sample region, and on a separate region of the chip, can also include the measurement circuitry. This configuration will minimize the associated stray resistances of the circuit structures.

Figure 18:
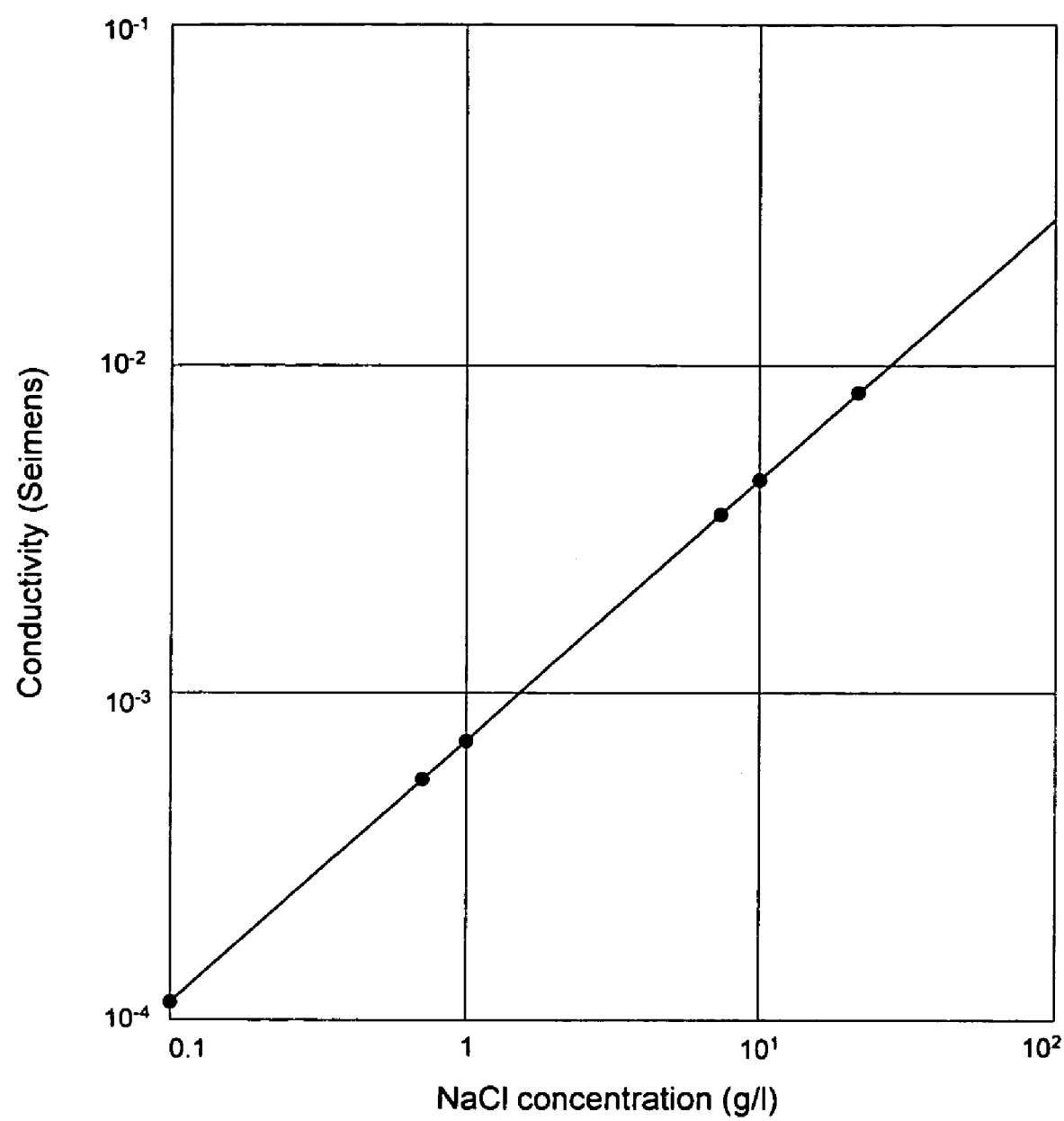
FIG. 18 illustrates a calibration curve relating the sodium content of the sample fluid with electrical conductivity.

In the FIG. 7 embodiment, the processing unit 704 produces signal waveforms at a single frequency, such as 100 kHz and 10 Volts peak-to-peak. The processing circuitry 704 then determines the osmolarity value from the sodium content correlated to the electrical conductivity using a calibration curve, such as the curve shown in FIG. 18. In this case, the calibration curve is constructed as a transfer function between the electrical conductivity (voltage) and the osmolarity value (i.e., the sodium content). It should be noted, however, that other calibration curves can also be constructed to provide transfer functions between other energy properties and the osmolarity value. For example, the variance, autocorrelation and drift of the signal can be included in an osmolarity calculation. If desired, the osmolarity value can also be built upon multi-variable correlation coefficient charts or neural network interpretation so that the osmolarity value can be optimized with an arbitrarily large set of measured variables.

In an alternate form of the FIG. 7 embodiment, the processing unit 704 produces signal waveforms of a predetermined frequency sweep, such as 1 kHz to 100 kHz in 1 kHz increments, and stores the conductivity and variance values received from the set of electrode pairs at each frequency. The output signal versus frequency curve can then be used to provide higher order information about the sample which can be used with the aforementioned transfer functions to produce an ideal osmolarity reading.

As shown in FIG. 7, the base socket connector 710 receives the pins 708 of the chip 701 into corresponding sockets 711. The connector 710, for example, can supply the requisite electrical power to the processing circuitry 704 and electrodes of the chip. Thus, the chip 701 can include the sample region electrodes and the signal generator and processing circuitry necessary for determining osmolarity, and the output comprising the osmolarity value can be communicated off the chip via the pins 708 through the connector 710 and to a display readout.

If desired, the base connector socket 710 can include a Peltier layer 712 located beneath the sockets that receive the pins 708 of the chip 701. Those skilled in the art will understand that a Peltier layer comprises an electrical/ceramic junction such that properly applied current can cool or heat the Peltier layer. In this way, the sample chip 701 can be heated or cooled, thereby further controlling evaporation of the sample fluid. It should be apparent that evaporation of the sample fluid should be carefully controlled, to ensure accurate osmolarity values obtained from the sample fluid.

Figure 9:
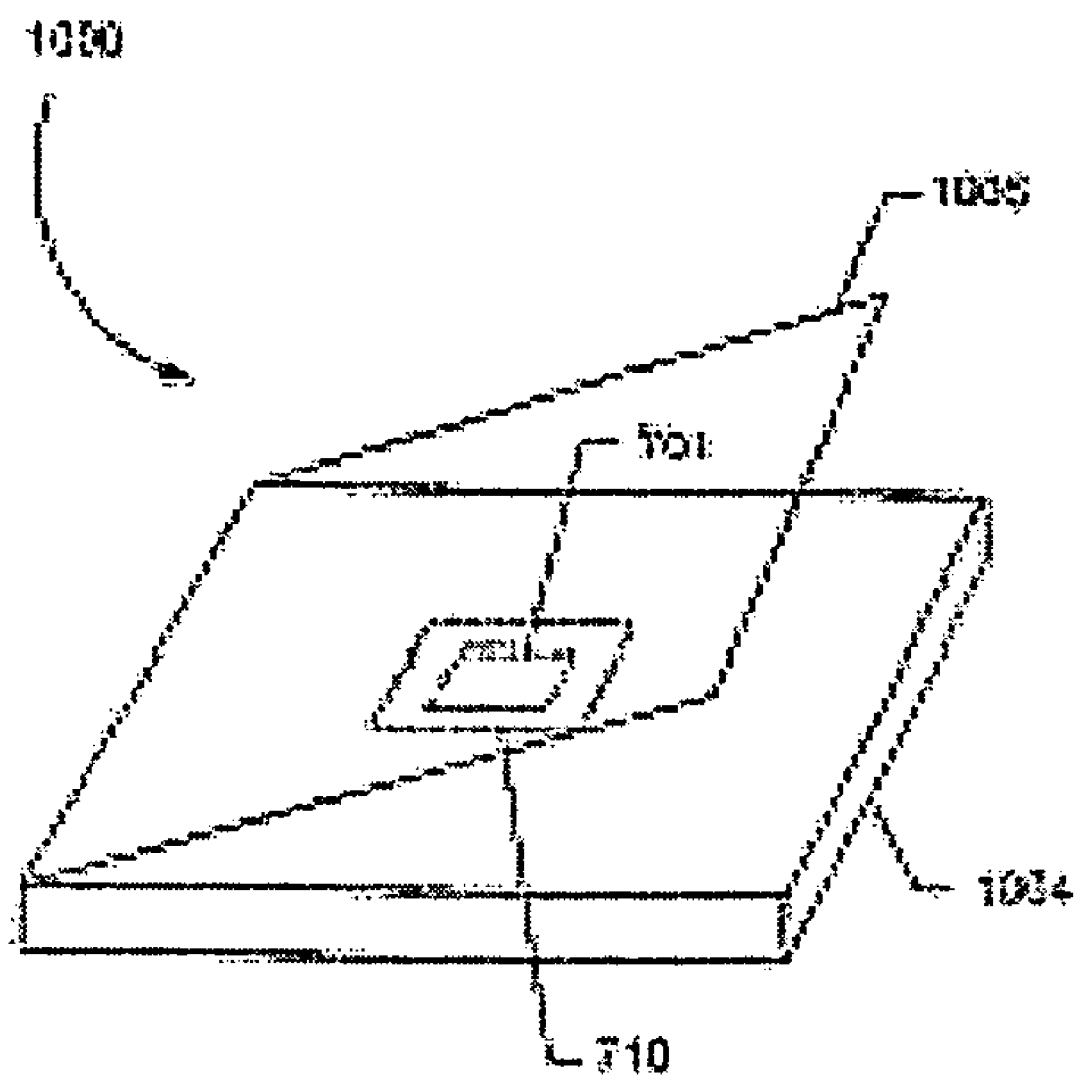
FIG. 9 illustrates a hinged base unit of the osmometer that utilizes the sample receiving chips described in FIGS. 1–5.

FIG. 9 shows an alternative embodiment of an osmometer in which the chip does not include an on-chip processing unit such as described above, but rather includes limited circuitry comprising primarily the sample region electrodes and interconnections. That is, the processing unit is separately located from the chip and can be provided in the base unit.

FIG. 9 shows in detail an osmometer 1000 that includes a base unit 1004, which houses the base connector 710, and a hinged cover 1006 that closes over the base connector 710 and a received measurement chip 701. Thus, after the sample fluid has been dispensed on the chip, the chip is inserted into the socket connector 710 of the base unit 1004 and the hinged cover 1006 is closed over the chip to reduce the rate of evaporation of the sample fluid.

It should be noted that the problem with relatively fast evaporation of the sample fluid can generally be handled in one of two ways. One way is to measure the sample fluid voltage quickly as soon possible after the droplet is placed on the sample region of the chip. Another way is to enable the measuring unit to measure the rate of evaporation along with the corresponding changes in conductivity values as described above. The processing unit can then post-process the output to estimate the osmolarity value. The processing can be performed in the hardware or in software stored in the hardware. Thus, the processing unit can incorporate different processing techniques such as using neural networks to collect and learn about characteristic of the fluid samples being measured for osmolarity, as well as temperature variations, volume changes, and other related parameters so that the system can be trained in accordance with neural network techniques to make faster and more accurate osmolarity measurements.

Figure 10:
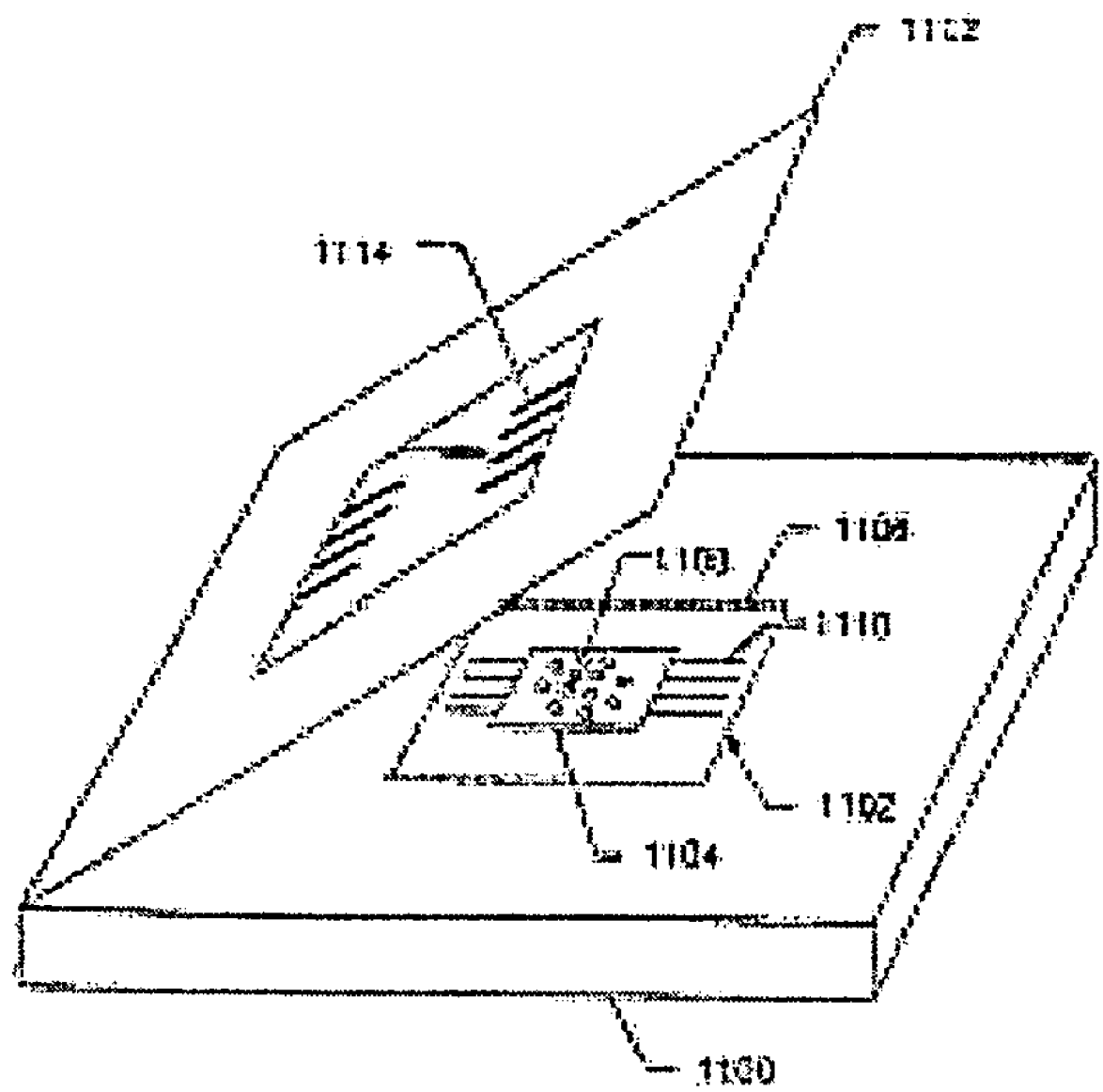
FIG. 10 illustrates a probe card configuration for the sample receiving chip and processing unit.

FIG. 10 shows another alternative construction, in which the osmolarity system utilizes a sample receiving chip 1102, that does not include IC packaging such as shown in FIG. 7. Rather, the FIG. 10 measurement chip 1102, is configured as a chip with an exposed sample region comprising the electrodes and associated connections, but the processing circuitry is located in the base unit for measuring the energy properties of the sample fluid. In this alternative construction, a connector similar to the connector socket 710 allows transmission of measured energy properties to the processing unit in the base unit. It will be understand that such a configuration is commonly referred to a probe card structure.

FIG. 10 shows a probe card base unit 1100 that receives a sample chip probe card 1102 that comprises a substrate 1104 with a sample region 1106 on which are formed electrodes 1108 that are wire bonded to edge connectors 1110 of the probe card. When the hinged lid 1112, of the base unit, is closed down over the probe card, connecting tines 1114 on the underside of the lid come into mating contact with the edge connectors 1110. In this way, the electrodes of the sample region 1106 are coupled to the processing circuitry and measurement can take place. The processing circuitry of the probe card embodiment of FIG. 10 can be configured in either of the configurations described above. That is, the processing to apply current to the electrodes and to detect energy properties of the sample fluid and determine osmolarity can be located on-chip, on the substrate of the probe card 1102, or off-chip, in the base unit 1100.

In all the alternative embodiments described above, the osmometer is used by placing a new measurement chip into the base unit while the hinged top is open. Upon placement into the base unit the chip is lowered up and begins monitoring its environment. Recording output signals from the chip at a rate of, for example, 1 kHz, will fully capture the behavior of the system. Placing a sample onto any portion of the electrode array generates high signal-to-noise increase in conductivity between any pair of electrodes covered by the sample fluid. The processing unit will recognize the change in conductivity as being directly related to the addition of sample fluid, and will begin conversion of electronic signals into osmolarity data once this type of change is identified. This strategy occurs without intervention by medical professionals. That is, the chip processing is initiated upon coupling to the base unit and is not dependent on operating the lid of the base unit or any other user intervention.

In any of the configurations described above, either the "smart chip" with processing circuitry on-chip (FIG. 7), or the electrode-only configuration with processing circuitry off-chip (FIG. 9), in a packaged chip (FIG. 7) or in a probe card (FIG. 10), the sample receiving chip can be disposed of after each use, so that the base unit serves as a platform for interfacing with the disposable measurement chip. As noted, the base unit can also include relevant control, communication, and display circuits (not shown), as well as software, or such features can be provided off-chip in the base unit. In this regard, the processing circuitry can be configured to automatically provide sufficient power to the sample region electrodes to irreversibly oxidize them after a measurement cycle, such that the electrodes are rendered inoperable for any subsequent measurement cycle. Upon inserted a used chip into the base unit, the user will be given an indication that the electrodes are inoperable. This helps prevent inadvertent multiple use of a sample chip, which can lead to inaccurate osmolarity readings and potentially unsanitary conditions.

A secondary approach to ensure that a previously used chip is not placed back into the machine includes encoding serial numbers, or codes directly onto the chip. The base unit will store the used chip numbers in memory and cross-reference them against new chips placed in the base connector. If the base unit finds that the serial number of the used chip is the same as an old chip, then the system will refuse to measure osmolarity until a new chip is inserted. It is important to ensure use of a new chip for each test because proteins adsorb and salt crystals form on the electrodes after evaporation has run its course, which corrupt the integrity of the measuring electrodes.

Figure 11:
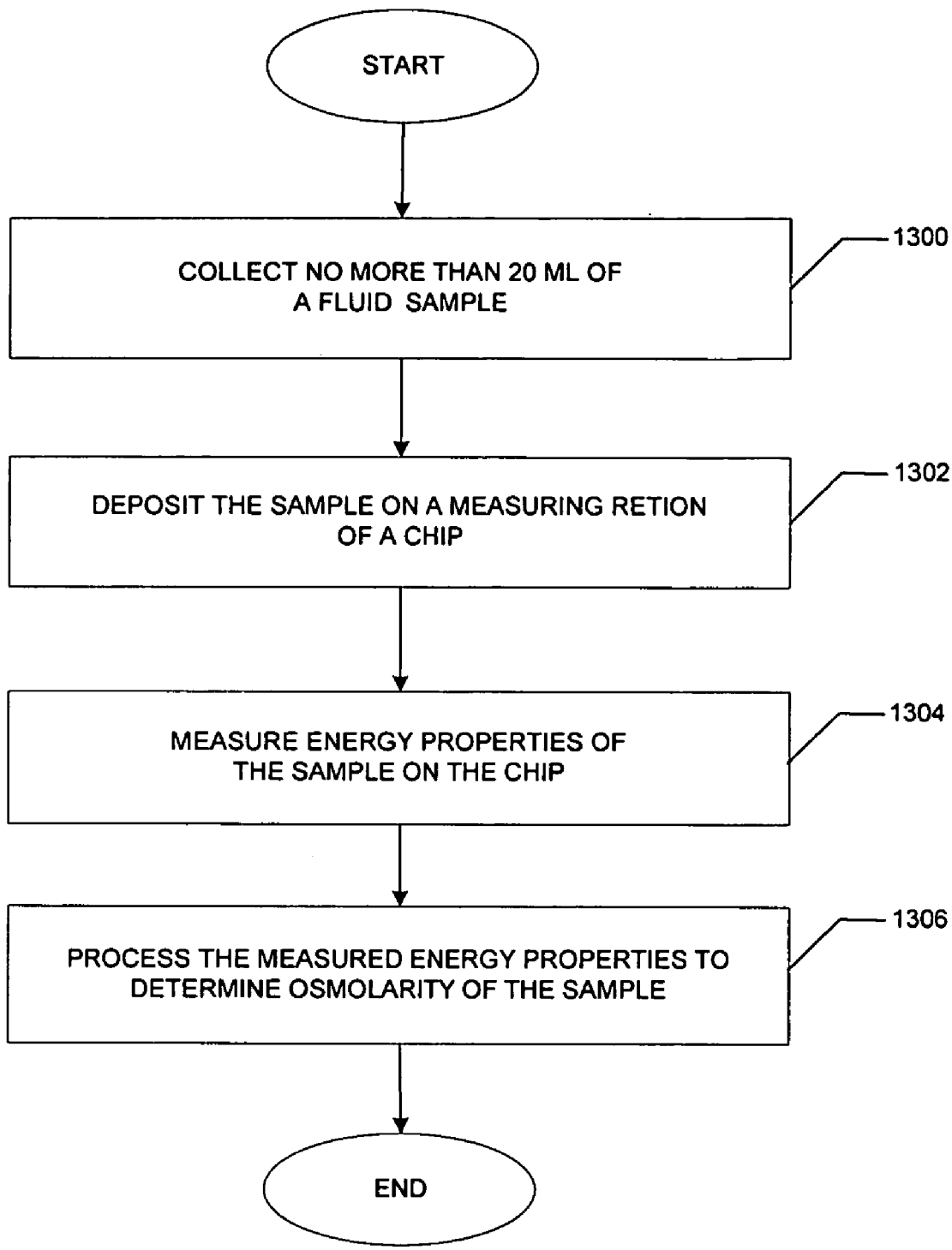
FIG. 11 is a flowchart describing an exemplary osmolarity measurement technique in accordance with the invention.

FIG. 11 is a flowchart describing an exemplary osmolarity measurement technique in accordance with the invention. A body fluid sample, such as a tear film, is collected at box 1300. The sample typically contains less than one microliter. At box 1302, the collected sample is deposited on a sample region of the chip substrate. The energy properties of the sample are then measured at box 1304. The measured energy properties are then processed, at box 1306, to determine the osmolarity of the sample. If the chip operates in accordance with electrical conductivity measurement, then the measurement processing at box 1306 can include the "electrode oxidation" operation described above that renders the chip electrodes inoperable for any subsequent measuring cycles.

In the measurement process for a conductivity measuring system, a substantially instantaneous shift is observed from the open circuit voltage to a value that closely represents the state of the sample at the time of collection, upon placement of a sample tear film on an electrode array of the substrate. Subsequently, a drift in the conductivity of the sample will be reflected as a continual change in the output.

The output of the measurement chip can be a time-varying voltage that is translated into an osmolarity value. Thus, in a conductivity-based system, more information than just the "electrical conductivity" of the sample can be obtained by measuring the frequency response over a wide range of input signals, which improves the end stage processing. For example, the calibration can be made over a multiple frequencies (e.g., measure ratio of signals at 10, 20, 30, 40, 50, 100 Hz) to make the measurement process a relative calculation. This makes the chip-to-chip voltage drift small. The standard method for macroscale electrode based measurements (i.e. in a pH meter, or microcapillary technique) is to rely upon known buffers to set up a linear calibration curve. Because photolithography is an extremely reproducible manufacturing technique, when coupled to a frequency sweep, calibration can be performed without operator intervention.

Again referring back to FIG. 7, the processing circuitry 704 applies a signal waveform to the sample region electrodes. The processing circuitry also receives the energy property signals from the electrodes and determines the osmolarity value of the sample fluid. For example, the processing unit receives electrical conductivity values from a set of electrode pairs. In one embodiment, the processing circuitry can be configured to receive sample data spaced over time. This collection of samples may be used to determine any relevant electrical characteristic of the fluid sample. In so doing, the system can be configured to perform two steps to aid in determining an osmolarity measurement using the plurality of samples. First, the system can determine the sample, or point at which the fluid was placed into the system. Second, the system can determine the signal strength at the point of placement, which must be done indirectly.

Figure 12:
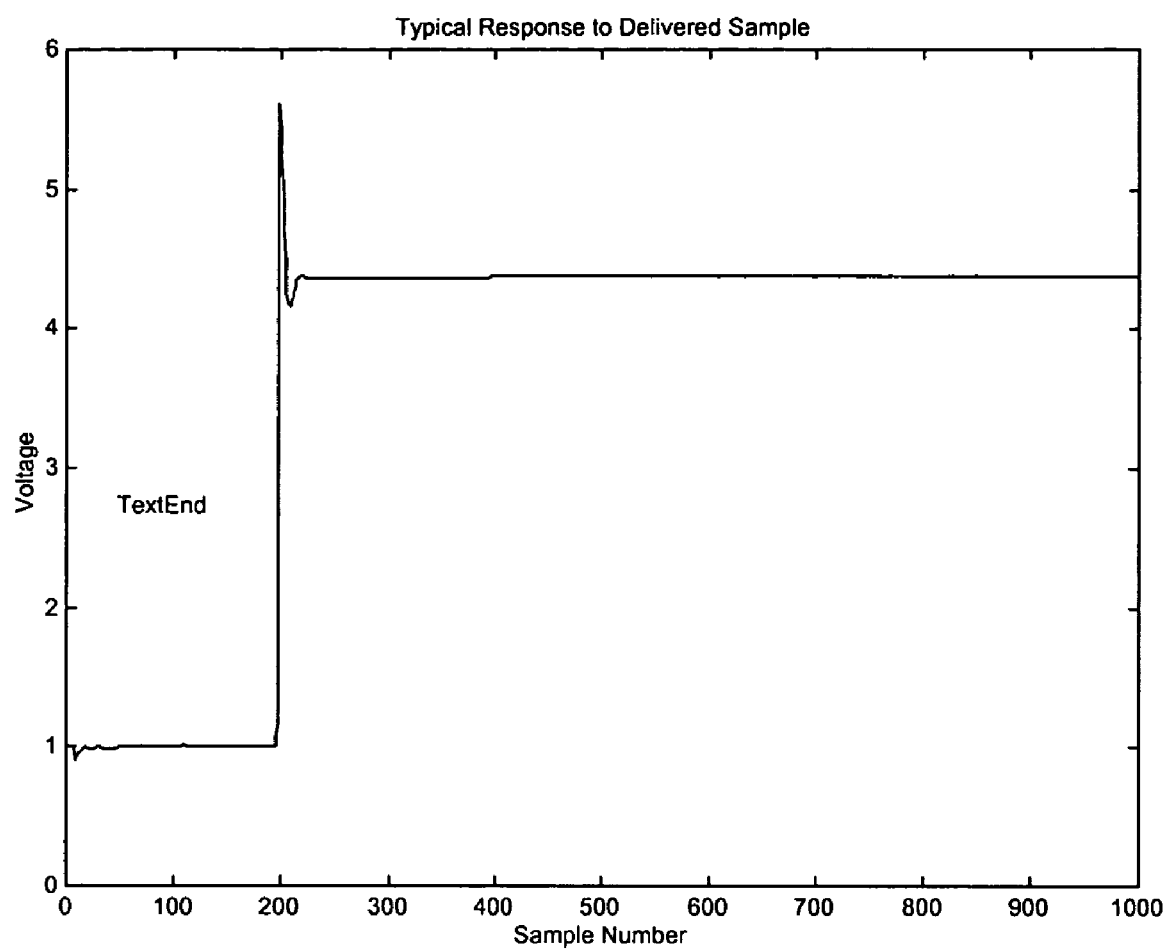
FIG. 12 is a graph illustrating the electrical conductivity of a sample of fluid.

FIG. 12, for example, depicts a typical graph of a signal waveform resulting from the placement of a sample fluid on, e.g., a measurement chip such as those described above. The graph of FIG. 12 depicts voltage versus time, as measured by samples taken of the electrical properties of a sample fluid. The point of placement is the point at which the signal spikes. From a computational standpoint, this point can be located by taking the derivative of the voltage signal. This point will be the point with the largest derivative.

There are several subtle, yet important characteristics of FIG. 12 that relate to the methods described herein for calculating osmolarity. The first is that there are two steady states. The far left side of the graph represents the open source voltage drop due to the function generator, electrodes, and other system components. The far right steady state is the summed response of the fluidic component and the inherent system components. Conceptually, in order to determine osmolarity, the value for the right hand steady state would be determined as would a value for the left hand steady state. The value for the left hand steady state can then be subtracted from the value of the right hand steady state, yielding a value that is representative of the response from the sample that was introduced. Using an appropriate algorithm, or other method, the resulting value can then be correlated, or converted, to an osmolarity measurement. This process is generally described below.

Clearly, the ability to identify the left hand steady state, and the right hand steady state is necessary in order to determine osmolarity. A human inspector can clearly demarcate the two regions and choose representative values in the steady states that can then be used to reconstruct the osmolarity; however, to a computer or processing system, these regions aren't obviously separated. This is true especially if the sample rate is too low to adequately capture the dynamics of the fluid drop.

FIG. 12 demonstrates the typical Vrms of a signal across a nanoliter volume in series with a ≈250 Ω potentiometer at 100 kHz, 10 V peak to peak. The fluidic sample in this example was prepared by measuring ≈2.9 grams of NaCl dissolved into 250 mL of deionized H2O, giving approximately a 200 mM (equivalent to a 400 mOsm) solution.

The total conductivity of the fluid portion of the circuit can be estimated by forming a ratio between the steady state voltage and the total voltage as described by the following equation, where V1 is the drop across the fluid, and Vtot represents the root mean squared voltage of the input wave:

$$V1=(R1/(R1+R2))Vtot$$

Solving for R1:

$$R1=(R2*V1/Vtot)/(1-(V1/Vtot))$$

After subtracting the initial bias voltage from the steady state voltage, as described above, a value for R1 of 127.3 Ω, or 0.0079 mho, can be obtained. Using the calibration curve shown in FIG. 18, the corresponding conductivity is shown to be roughly equivalent to a solution of 11.8 grams per liter NaCl, or an actual value of 406 mOsms.

The discrepancy between the hand-prepared sample and the conductivity based measurement of osmolarity, i.e., 6 mOsms, demonstrates the precision with which conductivity is capable of discerning different concentrations of ions. The error incurred by hand measuring the sodium chloride, using a graduated cylinder for volume measurement, and storage of the sample at room temperature introduces a far greater variance than the electrical error. Accordingly, conductivity can clearly distinguish very subtle changes and generate highly accurate osmolarity measurements when used as described herein.

Figure 13:
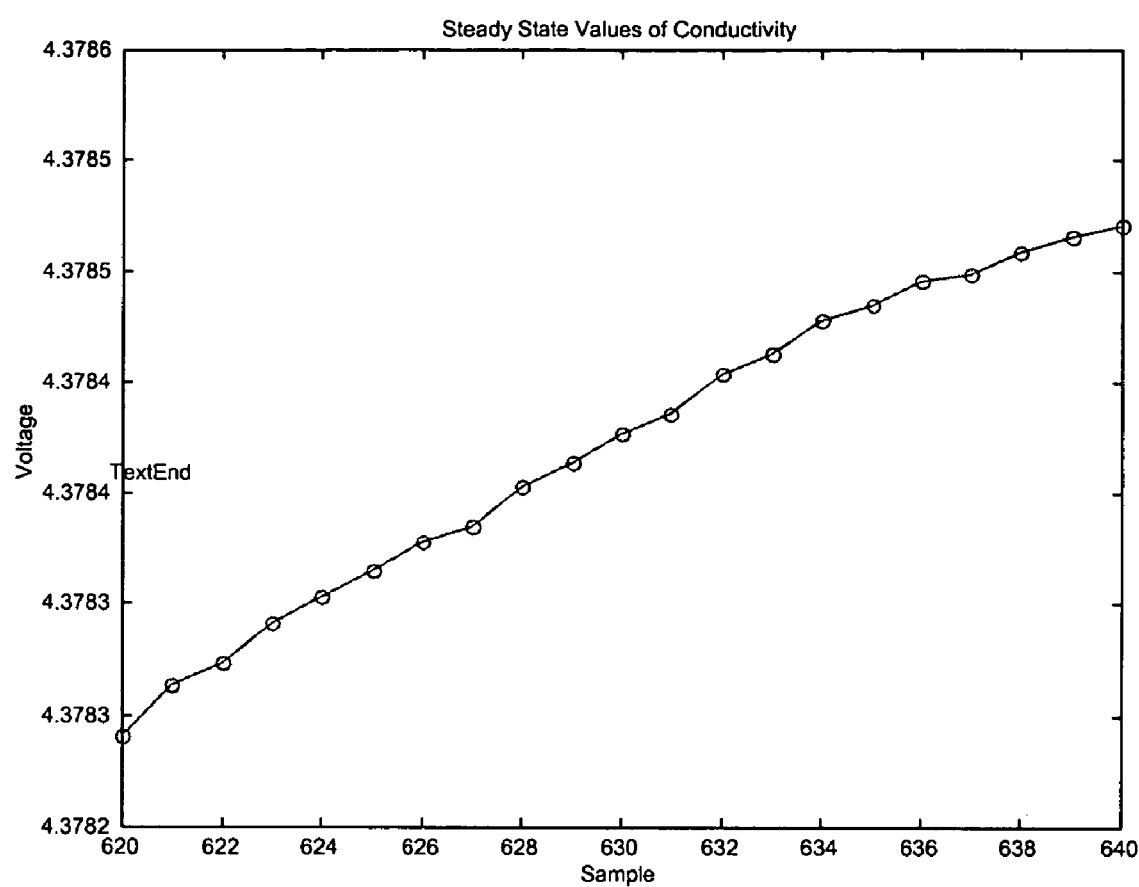
FIG. 13 illustrates the graph of FIG. 12 on a smaller scale such that the effects of evaporation can be seen.

But as mentioned, the two regions depicted in FIG. 12 are not as easily discernable to a processing device as they are to the humane eye. This is because while it seems like there are two constant regions, the actual data is far from straight. FIG. 13 demonstrates that the curve actually is effected by evaporation as evidenced by the slope in the curve as seen on a smaller scale, which is due to the continual evaporation of the sample fluid. Because of this, the time window on which samples are collected can be paramount to the interpretation of the osmolarity. In other words, in order to limit the effect of evaporation, it can be preferred to make a measurement of the right hand steady state nearer in time to placement of the sample. This, however, brings the corruptive signals associated with placement of the sample onto the measuring electrodes, which are described above, directly into play.

Figure 14:
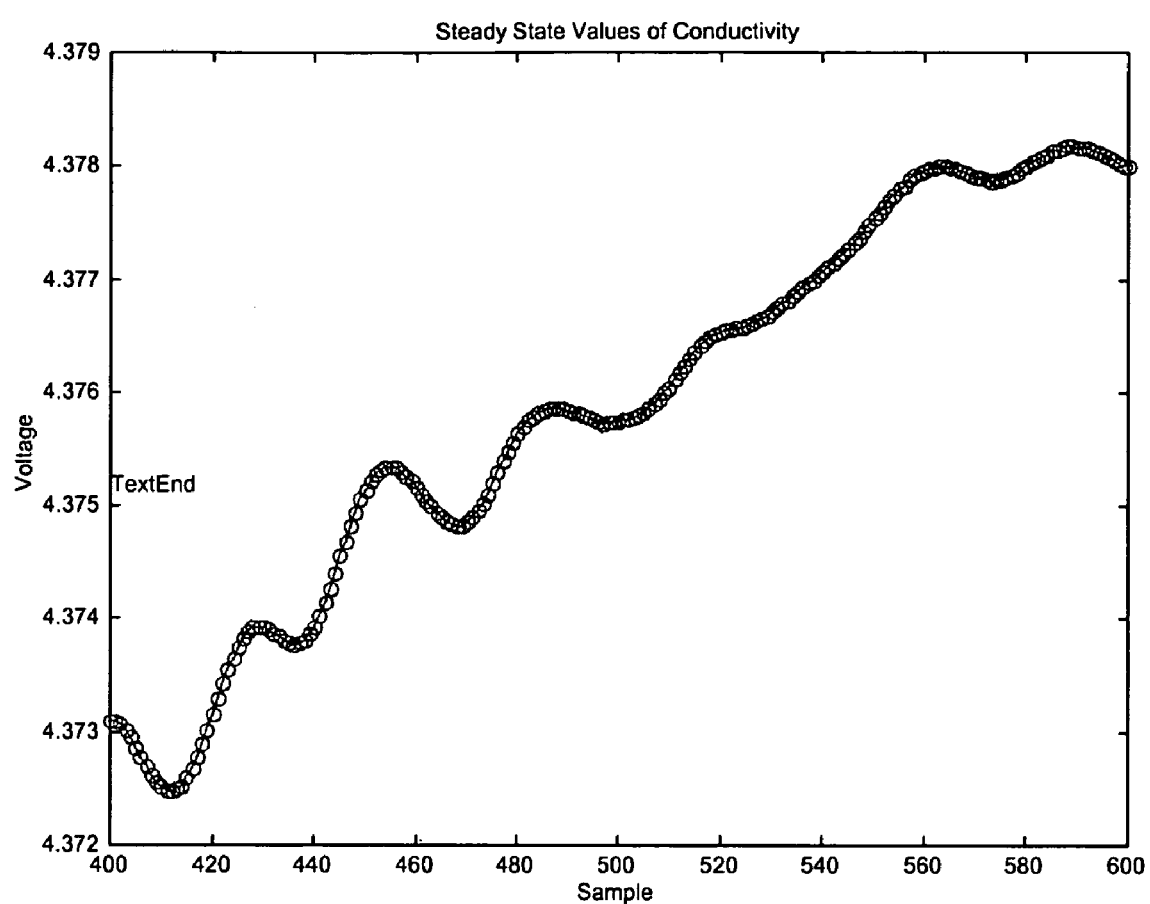
FIG. 14 shows another view of the graph of FIG. 12 on a still smaller scale.

In order to illustrate this point, FIG. 14 shows the data of FIG. 13 in an even smaller scale, from samples 400 to 600. While it is still apparent that the fluid is evaporating, it can now also be seen that the signal is not well behaved. The fluctuating, or oscillating, components imposed on the curve can be attributable to left over ringing that occurs when the sample is placed. Thus, in this respect, it is better to sample the right hand steady state far from the point of placement; however, as the sample evaporates, which can happen very rapidly, the osmolarity of the sample and the accompanying electrical characteristics will change. Obtaining the most accurate measurement, therefore, often requires that the characteristics of the sample at about the time of placement be determined.

Figure 15:
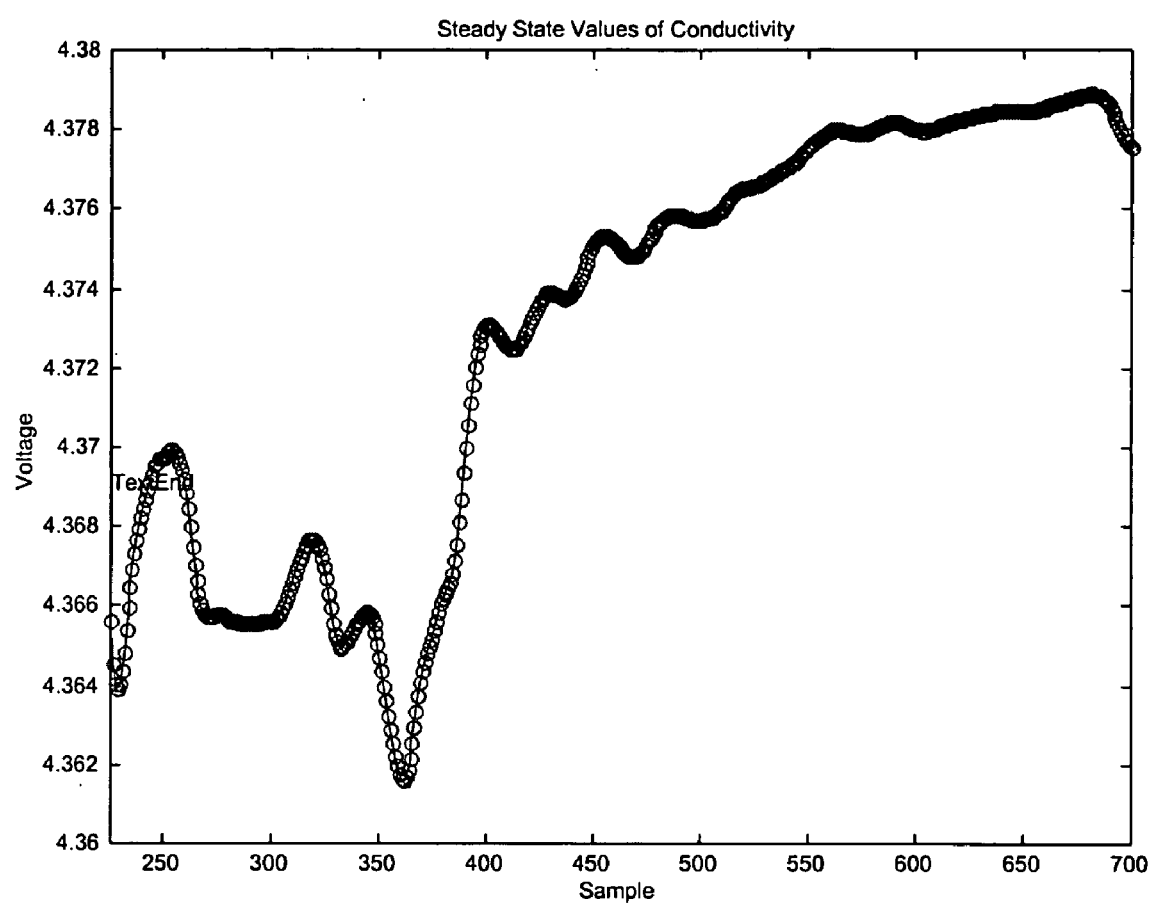
FIG. 15 illustrates a view of the graph of FIG. 12 near the point of placement varies.

But as shown in FIG. 15, the signal near the point of placement varies wildly due to the mechanical perturbations of the sample fluid when it is placed. As explained above, these perturbations are exacerbated by the presence of an air gap over the measuring electrodes. Thus, in order to enable inexpensive, and small measuring devices and still generate accurate measurements, the corruptive nature of the signal near the point of placement must be dealt with and overcome. Therefore, to determine the osmolarity of the sample at the time of placement, the system can be configured to fit a curve to the right hand steady state, which is not steady at all on the scale of interest, and extrapolate the curve back to the point at which the signal was placed. It should also be kept in mind that to achieve highly accurate measurements, the effects of evaporation should also be accounted for.

FIG. 15 makes clear that use of the data near the point of placement can skew the result and decrease the accuracy of the ultimate osmolarity calculation. Therefore, it is desirable to skip this data and fit the curve to the rest of the data. Any method of skipping the initial data may be used, but two specific embodiments are discussed below.

A first method for determining which data to skip is to determine a typical amount of data that should be skipped and hard code this amount into the measurement system. This method could be implemented in a variety of ways, including a static buffer or a static variable in the software written for the device.

Such an approach, however, can skip too much or too little data, thereby reducing the precision of the osmolarity measurement. It can therefore be desirable to be able to calculate an appropriate amount of data for each measurement made by a given device. For example, it may be determined that the resonating signal would no longer have a great effect if its amplitude were two percent or less of the maximum amplitude. With this requirement in mind, the system can then be configured to calculate the time required for the resonating signal to diminish to such a level.

One can clearly see in the successive closeups of the data illustrated in FIG. 13-FIG. 15 that any regression applied can be badly skewed by the initial post-drop dynamic response. The difference in voltage between a good fit and the bad fit can, for example, be about 0.02 V, or less than one half a percent. As noted above, use of a static buffer should suffice in most cases to fit the regression to only the steady state data, but for exceedingly small fluid samples, an alternate method is to fit the dynamics precisely and find out when the steady state begins.

A good model of the post drop response is a typical second order, underdamped relaxation:

$v\text{post fluid placement} = v\max e^{-at} \cos \beta t + (1/\beta) \cdot (aV^{max} + I_{max}/C) \cdot e^{-at} \sin \beta t$ The transfer function for this type of response, i.e. for a general second order system is:

$$G(s) = \frac{\omega_n^2}{s^2 + 2\xi\omega_n s + \omega_n^2}$$

For the underdamped response above, the system has two imaginary poles. A model of the step response in time of the fluid drop is of interest, as it contains an inherent resistance, capacitance, and inductance. Adding a pole to the G(s), equivalent to multiplying by (1/s), expanding by partial fractions and taking the Inverse Laplace transform results in:

$$c(t) = 1 - \frac{1}{\sqrt{1-\xi^2}} e^{-\xi\omega_n t} \cos\left(\omega_n \sqrt{1-\xi^2} t - \phi\right)$$

$$\phi = \tan^{-1}\left(\xi\sqrt{1-\xi^2}\right)$$

Accordingly, the settling time Ts, is defined as the time required for the amplitude of the decaying sinusoidal character to fall below two percent of the maximum value:

$$T_s = \frac{-\ln\left(0.02\sqrt{1-\xi^2}\right)}{\xi\omega_n}$$

Figure 16:
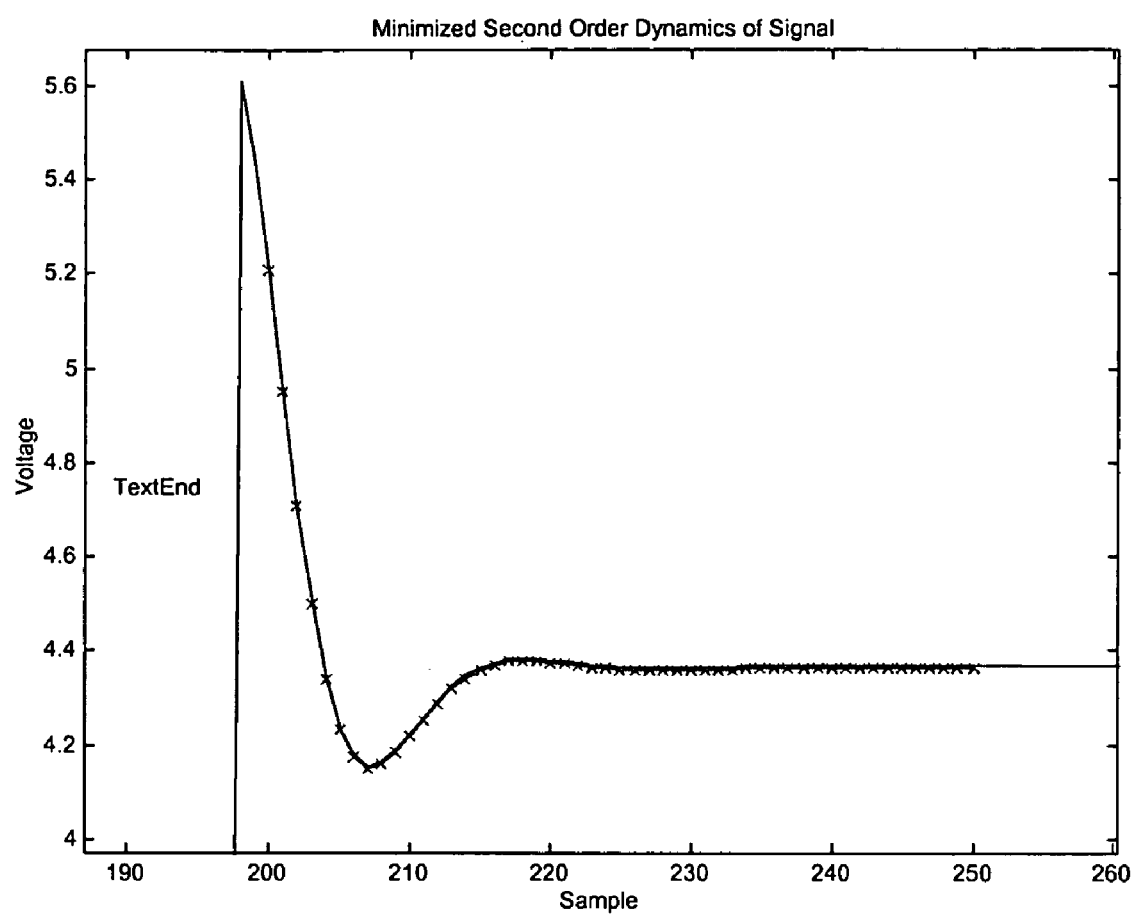
FIG. 16 shows the result of a multivariate minimization to fit the post drop dynamics of the graph illustrated in FIG. 12.

For the signal of interest, FIG. 16 shows the result of a multivariate minimization along Z and $W_n$ to fit the post drop dynamics.

Figure 17:
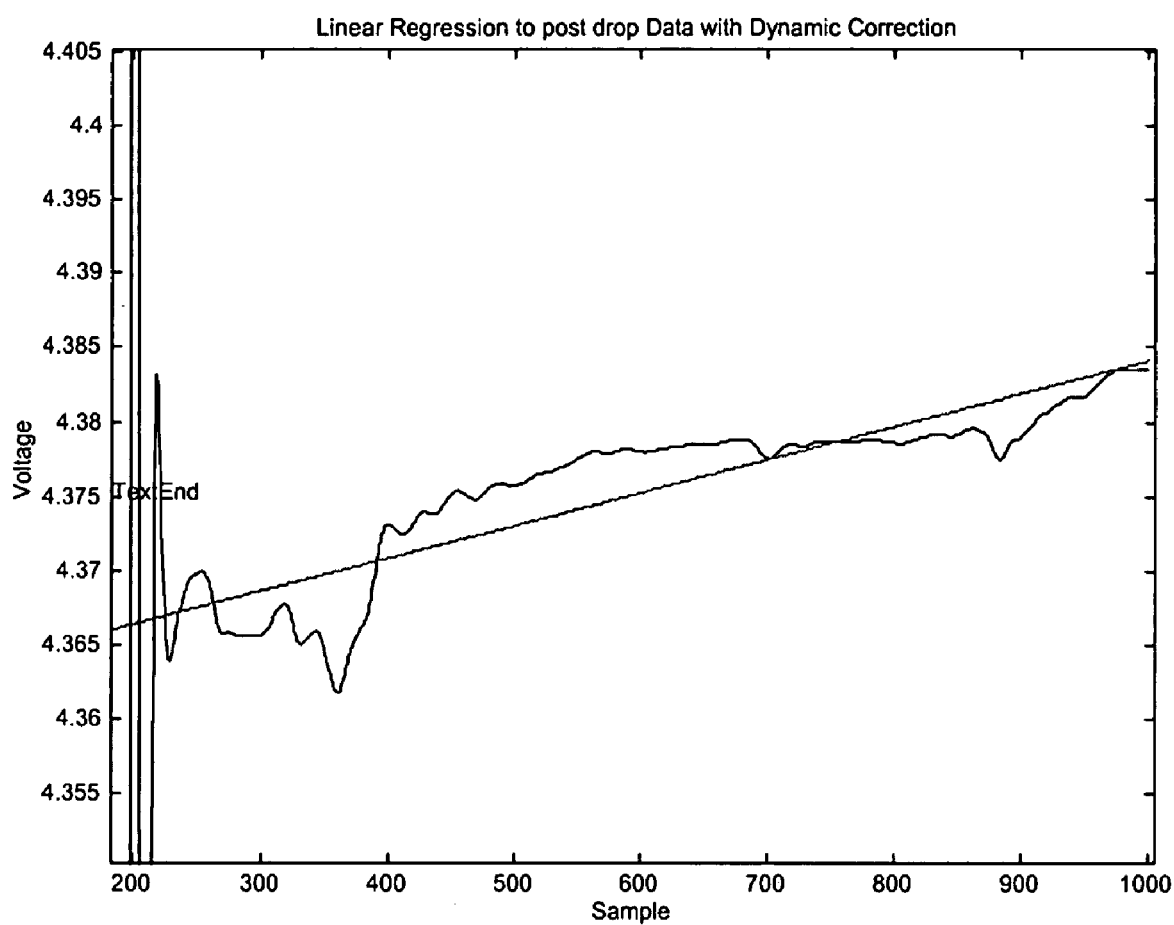
FIG. 17 illustrates a process for fitting a curve to the graph of FIG. 12.

Here, the resulting Ts is 12 samples. Adjusting for this dynamic behavior, it can be seen that the improvement in the linear regression as an approximation of evaporative effects in FIG. 17. The result of doing dynamic fitting to determine the actual steady state allows the sampling interval to be abstracted, resulting in a more precise overall estimate of the evaporative effects.

Thus, the systems and methods just described can be important when considering the various time and length scales at which the nanoliter signal is observed. Very small samples critically evaporate shortly after the post-drop dynamics have faded. Therefore, determining the optimal window of interest can be of paramount importance to the measurement of nanoliters of fluid.

Figure 19:
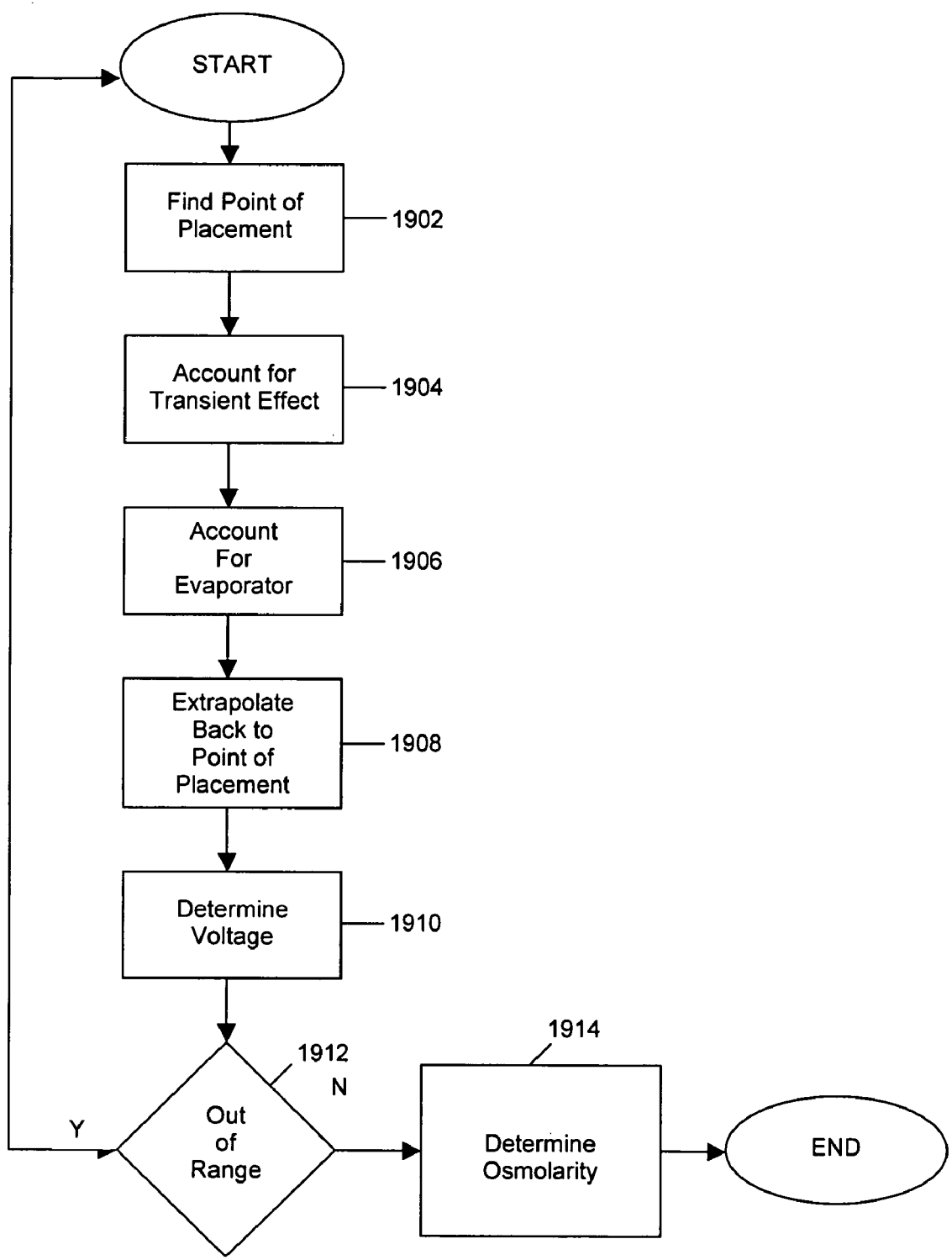
FIG. 19 is a flow chart illustrating another example method for determining osmolarity.

FIG. 19 is a flow chart illustrating another example method for determining osmolarity in accordance with the systems and methods described herein. First, in step 1902, the initial point of placement can be determined this can be determined using the derivative of the data as described above. Then, in step 1904, the effects of the transient response resulting after placement of the sample fluid can be accounted for. As mentioned above, this can comprise using a static interval, either preset, or determined based on properties associated with the resulting waveform.

Once the effect of the transient is accounted for in step 1904, then the effects of evaporation can be accounted for in step 1906 and the point of placement, or near to it, can be extrapolated in step 1908. The voltage associated with the point of placement can then be determined in step 1910 and used to determine the osmolarity in step 1914. As explained above, curve fitting techniques can be used to extrapolate to the point of placement, once the transient effects are accounted for.

As depicted by step 1912, extraneous results can be detected and eliminated in certain embodiments. Thus, once the voltage is determined in step 1910, the processing device can be configured to determine if the resulting voltage is way out of line with regard to an expected value or range. If it is, then the measurement can be ignored and the process can start over or be resumed. Neural networks, discussed a little more fully below, can for example be effectively used, e.g., using pattern matching techniques, to determine if a value should be discarded as being out of a normal expected range.

As just mentioned, the processing of the energy properties can be performed in a neural network configuration, where the seemingly disparate measured data points obtained from the energy properties can be used to provide more accurate osmolarity reading than from a single energy property measurement. Not only can such a neural network be configured to perform the regression techniques described in relation to FIGS. 12–17 to overcome corruptive signals, it can also be configured to provide other enhancements. For example, if only the electrical conductivity of the sample is measured, then the calibration curve of FIG. 18 can be used to simply obtain the osmolarity value corresponding to the conductivity. This osmolarity value, however, generally will not be as accurate as the output of the neural network.

The neural network can be designed to operate on a collection of calibration curves that reflects a substantially optimized transfer function between the energy properties of the sample fluid and the osmolarity. Thus, in one embodiment, the neural network constructs a collection of calibration curves for all variables of interest, such as voltage, evaporation rate and volume change. The neural network can also construct or receive as an input a priority list that assigns an importance factor to each variable to indicate the importance of the variable to the final outcome, or the osmolarity value. The neural network constructs the calibration curves by training on examples of real data where the final outcome is known a priori. Accordingly, the neural network will be trained to predict the final outcome from the best possible combination of variables. This neural network configuration that processes the variables in an efficient combination is then loaded into the processing unit residing in the measurement chip 701 or the base unit. Once trained, the neural network can be configured in software or hardware.

Although the embodiments described above for measuring osmolarity provides substantial advantage over the conventional osmolarity measuring techniques such as a freezing point depression technique, the teachings of the present invention can be used to determine osmolarity of a sample in accordance with the freezing point depression technique. Accordingly, the exemplary osmometry system 600, of FIG. 6, can be used to provide an osmolarity value based on the freezing point depression technique.

The freezing point depression system involves collecting and depositing the sample fluid in a similar manner as in the boxes 1300 and 1302 of the flowchart in FIG. 11. As noted above, however, the osmometer of the osmometer system can include a cooling device, such as a Peltier cooling device. In the FIG. 7 embodiment described above, the Peltier device is disposed on the socket 710 or the chip 701 (see FIG. 7) to cool the sample. If desired, the Peltier cooling device can be used to cool the sample fluid to the freezing point of the sample fluid. A photo-lithographed metal junction, or p-n junction, known as a thermocouple, can be used to monitor the temperature of aliquot-sized samples. The thermocouple would operate in parallel to the electrode array and Peltier cooling device, where the chip would be cooled below freezing so that the sample becomes a solid. Upon solidification, the electrical conductivity of the sample will drastically change. Because the thermocouple is continually measuring the temperature, the point at which the conductivity spikes can be correlated to the depressed freezing point. Alternatively, the chip could be supercooled immediately prior to sample introduction by the Peltier unit, and then by using the resistive heating inherent to the electrodes, a current can be passed along the solid phase material. Upon melting, the conductivity will again drastically change. In the second measurement technique, it is likely that evaporation will be less of a factor. Thus, the present invention permits freezing point depression to be performed at significantly smaller volumes of sample fluid than previously possible.

While certain embodiments of the inventions have been described above, it will be understood that the embodiments described are by way of example only. Accordingly, the inventions should not be limited based on the described embodiments. Rather, the scope of the inventions described herein should only be limited in light of the claims that follow when taken in conjunction with the above description and accompanying drawings.

What is claimed:

1. A method of determining the osmolarity of a fluid sample, comprising:
   generating sample data for the fluid sample;
   accounting for transient effects in the sample data;
   determining a value associated with an initial point of placement for the sample fluid once the transient effects are accounted for;
   using the determined value to obtain an osmolarity measurement for the fluid sample; and
   accounting for the effects of evaporation before determining the value associated with the initial point of placement.

2. A method of determining the osmolarity of a fluid sample, comprising:
   generating sample data for the fluid sample;
   accounting for transient effects in the sample data;
   determining a value associated with an initial point of placement for the sample fluid once the transient effects are accounted for;
   using the determined value to obtain an osmolarity measurement for the fluid sample; and
   wherein the transient effect is due to mechanical relaxation of the fluid sample.

3. The method of claim 2, wherein accounting for mechanical relaxation comprises:
   determining the number of samples that it takes for the sample data to reach a steady state after the fluid sample is introduced; and
   fitting a curve to a portion of the sample data based on the determination of the number of samples that it takes for the sample data to reach a steady state after the fluid sample is introduced.

4. The method of claim 3, wherein determining the number of samples that it takes for the sample data to reach a steady state comprises using a fixed number of samples.

5. The method of claim 3, wherein determining the number of samples that it takes for the sample data to reach a steady state comprises determining the point at which the sample data settles into a steady state based on the sample data.

6. The method of claim 5, wherein determining the point at which the sample data settles into a steady state comprises determining the point at which the amplitude of the sample data falls below two percent of the maximum value.

7. The method of claim 5, wherein determining the point at which the signal waveform settles into a steady state is performed using a neural network.

8. A method of determining the osmolarity of a fluid sample, comprising:
   generating sample data for the fluid sample;
   accounting for transient effects in the sample data accounting for the effects of evaporation before determining the value associated with the initial point of placement;

determining a value associated with an initial point of placement for the sample fluid once the transient and evaporation effects are accounted for; and using the determined value to obtain an osmolarity measurement for the fluid sample.

9. The method of claim 8, further comprising determining the initial point of placement after the sample data is generated.

10. The method of claim 8, wherein using the determined value to obtain an osmolarity measurement comprises subtracting a baseline value from the determined value and using the resulting difference value to determine the osmolarity measurement.

11. The method of claim 10, wherein obtaining the osmolarity measurement comprises using the resulting difference to look up an osmolarity value based on a calibration curve.

12. The method of claim 8, wherein determining a value associated with the initial point of placement comprises fitting a curve to a portion of the sample data once the transient and evaporation effects are accounted for and extrapolating the value using the curve.

13. The method of claim 12, wherein fitting the curve to a portion of the sample data comprises performing a linear regression.

14. The method of claim 8, wherein the transient effect is due to mechanical relaxation of the fluid sample.

15. The method of claim 14, wherein accounting for mechanical relaxation comprises:

determining the number of samples that it takes for the sample data to reach a steady state after the fluid sample is introduced; and fitting a curve to a portion of the sample data based on the determination of the number of samples that it takes for the sample data to reach a steady state after the fluid sample is introduced.

16. The method of claim 15, wherein determining the number of samples that it takes for the sample data to reach a steady state comprises using a fixed number of samples.

17. The method of claim 15, wherein determining the number of samples that it takes for the sample data to reach a steady state comprises determining the point at which the sample data settles into a steady state based on the sample data.

18. The method of claim 17, wherein determining the point at which the sample data settles into a steady state comprises determining the point at which the amplitude of the sample data falls below two percent of the maximum value.

19. The method of claim 8, wherein determining the initial point of placement comprises taking the derivative of the signal waveform and finding the sample at which the derivative is at its maximum.

20. An osmolarity measurement system, comprising:

a measurement device configured to receive a fluid sample and generate sample data for the fluid sample; and a processing device coupled with the measurement device, the processing device configured to account for transient effects in the sample data, determine a value associated with an initial point of placement for the fluid sample once the transient effects are accounted for, and use the determined value to obtain an osmolarity measurement for the fluid sample, wherein the processing device is farther configured to account for the effects of evaporation before determining the value associated with the initial point of placement.

21. An osmolarity measurement system, comprising:

a measurement device configured to receive a fluid sample and generate sample data for the fluid sample; and a processing device coupled with the measurement device, the processing device configured to account for transient effects in the sample data, determine a value associated with an initial point of placement for the fluid sample once the transient effects are accounted for, and use the determined value to obtain an osmolarity measurement for the fluid sample, wherein the transient effect is due to mechanical relaxation of the fluid sample, and wherein the processing device is configured to account for mechanical relaxation by determining the number of samples that it takes for the sample data to reach a steady state after the fluid sample is introduced and fitting a curve to a portion of the sample data based on the determination of the number of samples that it takes for the sample data to reach a steady state after the fluid sample is introduced.

22. The osmolarity measurement system of claim 21, wherein determining the number of samples that it takes for the sample data to reach a steady state comprises using a fixed number of samples.

23. The osmolarity measurement system of claim 21, wherein determining the number of samples that it takes for the sample data to reach a steady state comprises determining the point at which the sample data settles into a steady stale based on the sample data.

24. The osmolarity measurement system of claim 23, wherein determining the point at which the sample data settles into a steady state comprises determining the point at which the amplitude of the sample data falls below two percent of the maximum value.

* * * * *